United States Patent
Page

(10) Patent No.: US 11,510,776 B2
(45) Date of Patent: *Nov. 29, 2022

(54) CAPSULAR TENSION RING INSERTER AND METHOD

(71) Applicant: Page Surgical Innovations, LLC, Bloomfield Hills, MI (US)

(72) Inventor: Timothy Patrick Page, Birmingham, MI (US)

(73) Assignee: Page Surgical Innovations, LLC, Birmingham, MI (US)

( * ) Notice: Subject to any disclaimer, the term of this patent is extended or adjusted under 35 U.S.C. 154(b) by 223 days.

This patent is subject to a terminal disclaimer.

(21) Appl. No.: 16/910,925

(22) Filed: Jun. 24, 2020

(65) Prior Publication Data

US 2020/0315785 A1 Oct. 8, 2020

Related U.S. Application Data

(63) Continuation of application No. 15/577,503, filed as application No. PCT/US2016/035068 on May 31, 2016, now Pat. No. 10,702,377.

(60) Provisional application No. 62/257,973, filed on Nov. 20, 2015, provisional application No. 62/167,456, filed on May 28, 2015.

(51) Int. Cl.
*A61F 2/16* (2006.01)
*A61F 2/14* (2006.01)

(52) U.S. Cl.
CPC ............ *A61F 2/1694* (2013.01); *A61F 2/148* (2013.01); *A61F 2/1664* (2013.01); *A61F 2/167* (2013.01)

(58) Field of Classification Search
CPC ...... A61F 2/148; A61F 2/1662; A61F 2/1664; A61F 2/167; A61F 2/1694
See application file for complete search history.

(56) References Cited

U.S. PATENT DOCUMENTS

| | | | |
|---|---|---|---|
| 4,349,027 A | 9/1982 | DiFrancesco |
| 4,852,566 A | 8/1989 | Callahan |
| 5,098,443 A | 3/1992 | Parel |
| 5,676,669 A | 10/1997 | Colvard |
| 5,843,184 A | 12/1998 | Cionni |
| 6,319,282 B1 | 11/2001 | Nishi |

(Continued)

FOREIGN PATENT DOCUMENTS

| | | |
|---|---|---|
| EP | 0512785 A1 | 11/1992 |
| WO | 2004041323 A2 | 5/2004 |
| WO | 2014138615 A1 | 9/2014 |

OTHER PUBLICATIONS

Ahmed, II. K. et al., "Optimal Timing of Capsular Tension Ring Implantation: Miyake-Apple Video Analysis", J. Cataract Refract. Surg., vol. 31, 2005, pp. 1809-1813.

(Continued)

*Primary Examiner* — Ryan J. Severson
(74) *Attorney, Agent, or Firm* — Howard & Howard Attorneys PLLC

(57) ABSTRACT

A capsular tension ring inserter (10) and method includes a cannula (54) adapted to house a capsular tension ring (CTR) (26) having a leading eyelet (32), a hook element (56) disposed within the cannula (54) that engages and moves the CTR (26) during deployment, and a suture (28) placed on the leading eyelet (32) and fed back through the cannula (54) to allow a user to control insertion of tile CTR (26) into a capsular bag (42) of an eye (40) by pulling on the suture (28) during insertion of the CTR (26).

16 Claims, 28 Drawing Sheets

(56) References Cited

U.S. PATENT DOCUMENTS

| | | |
|---|---|---|
| 6,413,277 B1 | 7/2002 | Neuhann |
| 6,749,631 B1 | 6/2004 | Pietrini et al. |
| 6,899,733 B2 | 5/2005 | Snyder |
| 7,806,929 B2 | 10/2010 | Brown |
| 8,721,654 B2 | 5/2014 | Page |
| 9,339,375 B2 | 5/2016 | Lee |
| 10,702,377 B2 | 7/2020 | Page |
| 2002/0091442 A1 | 7/2002 | Snyder |
| 2009/0018650 A1 | 1/2009 | Boxer Wachler |
| 2009/0054904 A1 | 2/2009 | Holmen |
| 2011/0082543 A1 | 4/2011 | Soll |
| 2011/0178527 A1 | 7/2011 | Page |
| 2012/0290086 A1 | 11/2012 | Malyugin et al. |
| 2016/0022488 A1 | 1/2016 | Dimmig |
| 2018/0132998 A1 | 5/2018 | Page |

OTHER PUBLICATIONS

Angunawela, RI, et al., "Fish-Tail Technique for Capsular Tension Ring Insertion", J. Cataract Refract. Surg., vol. 33, 2007, pp. 767-769.

Duckworth & Kent Ltd., "Capsule Tension Ring Inserter Webpage", http://www.duckworth-and-kent.com/products/product_details.asp?PROD_NUM=7-811& . . . , 2016, 2 pages.

FCI Ophthalmics, "Mackool Cataract Support System Webpage", http://www.fci-ophthalmics.com/cataract#mackool, 2015, 5 pages.

Frohn, Andreas et al., "Video—Safety Suture for CTR", vol. 17, Issue 4, Episode 5, http://eyetube.net/series/video-journal-of-cataract-and-refractive-surgery/video.asp?vol=17&iss=4&f=bupoz, 2017, 3 pages.

Hara, T. et al., "'Equator Ring' for Maintenance of the Completely Circular Contour of the Capsular Bag Equator After Cataract Removal", Opthalmic. Surg., vol. 22, 1991, pp. 358-359.

Hasanee, K. et al., "Capsular Tension Rings and Related Devices: Current Concepts", Curr. Opin. Ophthalmol., vol. 17, 2006, pp. 31-41.

International Search Report for Application No. EP16800855.5; dated Nov. 13, 2018; 8 pages.

International Search Report of PCT/US2016/35068, dated Sep. 2, 2016; 2 pages.

Jacob, S. et al., "Efficacy of a Capsular Tension Ring for Phacomulsification in Eyes with Zonular Dialysis", J. Cataract. Refract. Surg., vol. 29, 2003, pp. 315-321.

Jacob, S. et al., "Glued Capsular Hook: Technique for Fibrin Glue-Assisted Sutureless Transscleral Fixation of the capsular Bag in Subluxated Cataracts and Intraocular Lenses", J. Cataract. Refract. Surg., vol. 40, 2014, pp. 1958-1965.

Kurz, S. et al., "Spring Constants of Capsular Tension Rings", J. Cataract Refract. Surg., vol. 30, 2004, pp. 1993-1997.

Morcher GMBH, "Capsular Tension Rings Webpage", https://www.morcher.com/nc/en/products/capsular-rings.html, 2015, 16 pages.

Moreno-Montanes, J. et al., "Extraction of Endocapsular Tension Ring After Phaoemulsification in Eyes With Pseudoexfoliation", Am. J. Ophthalmol., vol. 138, 2004, pp. 173-175.

Page, MD, Timothy, Suture-Guided Capsular Tension Ring Insertion to Reduce Risk for Iatrogenic Zonular Damage, J. Cataract Refract. Surg., vol. 41, 2015, pp. 1564-1567.

Riedel, PJ et al., "Capsular Tension Rings", Colvard DM, ed., Achieving Excellence in Cataract Surgery; a Step-By-Step Approach, Los Angeles, CA, 2009, pp. 115-121.

CAPSULAR TENSION RING INSERTER AND METHOD

CROSS-REFERENCE TO RELATED APPLICATION(S)

The present application is a continuation of U.S. patent application Ser. No. 15/577,503, filed on Nov. 28, 2017, now U.S. Pat. No. 10,702,377, which claims the benefit of U.S. Provisional Patent Application Ser. No. 62/167,456, filed May 28, 2015 and U.S. Provisional Patent Application Ser. No. 62/257,973, filed Nov. 20, 2015, the entire disclosure of each is hereby incorporated by reference.

BACKGROUND OF THE INVENTION

1. Technical Field

The present invention relates generally to capsular tension rings and, more particularly, to a capsular tension ring inserter and method.

2. Description of the Related Art

Capsular tension rings (CTRs) are approved by the U.S. Food and Drug Administration to assist in placing and centering an intraocular lens (IOL). Capsular tension rings have since become invaluable tools for the management of compromised zonular fibers during cataract surgery. A CTR is often used in cases with weak zonular fibers due to pseudoexfoliation, ocular trauma, Marfan syndrome, hypermature cataracts, and other etiologies that may result in weak zonular fibers. Since the initial introduction of the CTR, several modifications have evolved to allow endocapsular implantation of an intraocular lens (IOL) depending upon the surgeon's assessment of the compromised zonular fibers.

A CTR works by creating tension within a capsular bag to support an area of zonular weakness via recruitment of the surrounding intact zonular fibers. A CTR is referred to as having 2 diameters, one in the open and the other in the compressed state. For example, a CTR used for normal to myopic eyes has an open diameter of 13.0 mm and a compressed diameter of 11.0 mm. Because the diameter of the open CTR is greater than the diameter of the capsular bag, tension will occur across the capsular bag recruiting the strength of the intact zonular fibers. The CTR automatically expands as it enters the fornix of the capsular bag to its largest possible diameter based on its size and spring constant.

Complications may occur as the CTR is inserted into the capsular bag as torque is created at the point of contact between the CTR and the capsular bag, potentially resulting in extension of a zonular dialysis or creating an iatrogenic dialysis. Capsular tension ring insertion has been proven to produce zonular stress and elongation with capsular bag displacement ranging from 0.5 mm to 4.0 mm depending upon the tinning of insertion of the CTR.

Techniques to mitigate CTR complications associated with implantation have been described in the literature. One such solution describes a safety suture placed in the leading eyelet for CTR insertion prior to phacoemulsification to serve as a rescue technique in the event of a posterior capsular rupture. If the capsular bag were to rupture during surgery, the CTR may be removed with the suture in the leading eyelet. Another known solution is the "fish tail technique" method for CTR insertion to reduce the risk of extending a dialysis. Subsequently, a modification called the "fishtail on a line technique" was developed to prevent over bending of the CTR in a fishtail technique. However, the fishtail technique, or later modifications, alter the form of the intended insertion design and do not give the surgeon direct control of the leading eyelet as it passes through areas of potential capsular entanglement.

SUMMARY OF THE INVENTION

The present invention provides a capsular tension ring inserter including a cannula housing a capsular tension ring (CTR) having a leading eyelet, an element disposed within the cannula that engages and moves the CTR during deployment, and a suture placed on the leading eyelet and fed back through the cannula to allow a user to control insertion of the CTR into a capsular bag of an eye by pulling on the suture during insertion of the CTR.

Further, the present invention provides a capsular tension ring inserter including a capsular tension ring (CTR) having a leading eyelet, a cannula housing the CTR, an element disposed within the cannula that engages and moves the CTR during deployment, and a pre-loaded suture on the leading eyelet and the cannula to allow a user to control insertion of the CTR into a capsular bag of an eye by pulling on the suture during insertion of the CTR. It should be appreciated that the CTR inserter may also be designed so that a suture may not be pre-loaded, but added at the surgeon's discretion utilizing a port or clip configuration on the CTR inserter.

In addition, the present invention provides a method of operating a capsular tension ring inserter including a capsular tension ring (CTR) inserter including a cannula that houses a capsular tension ring (CTR) having a leading eyelet and an element disposed within the cannula that engages and moves the CTR during deployment with a suture placed on the leading eyelet, and comprising the steps of: moving the CTR to a partially deployed position, and controlling the leading eyelet with the suture during insertion of the CTR into a capsular bag of an eye by allowing a user to pull on the suture during insertion of the CTR.

One advantage of the present invention is that a capsular tension ring (CTR) inserter and method of operating the capsular tension ring inserter are provided as a simple technique that uses a suture to mitigate the potential complications that may occur during CTR insertion into a capsular bag of an eye. Another advantage of the present invention is that the CTR inserter and method maintains the intended shape and direction of implantation. Yet another advantage of the present invention is that the CTR inserter and method enables precise control of the leading eyelet of the CTR, thereby reducing the risk for capsule entanglement and iatrogenic zonular dialysis. An additional advantage of the present invention is that the suture serves as an indicator for the position of the leading eyelet that is otherwise hidden under the iris, enabling the surgeon to help recognize CTR entanglement within the capsular bag.

Other objects, features, and advantages of the present invention will be readily appreciated as the same becomes better understood by reference to the following detailed description when considered in connection with the accompanying drawings.

DETAILED DESCRIPTION OF TILE PREFERRED EMBODIMENT(S)

Figure 1:
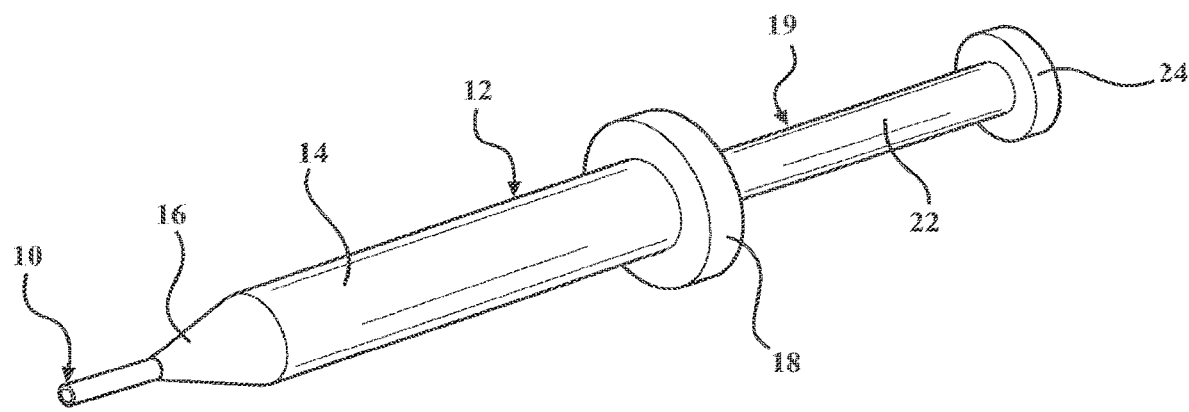
FIG. 1 is a perspective view of one embodiment of a CTR inserter, according to the is present invention, illustrated in operational relationship with a syringe.

The embodiments below are described with reference to the drawings in which like elements are referred to with like terms and/or numerals. The relationship and functioning of the various elements of the embodiments are better understood by the following detailed description. However, the embodiments as described below are by way of example only, and the present invention is not limited to the embodiments illustrated in the drawings. It should also be understood that the drawings are not drawn to scale and, in certain instances, details which are not necessary for an understanding of the embodiments have been omitted.

Figure 28:
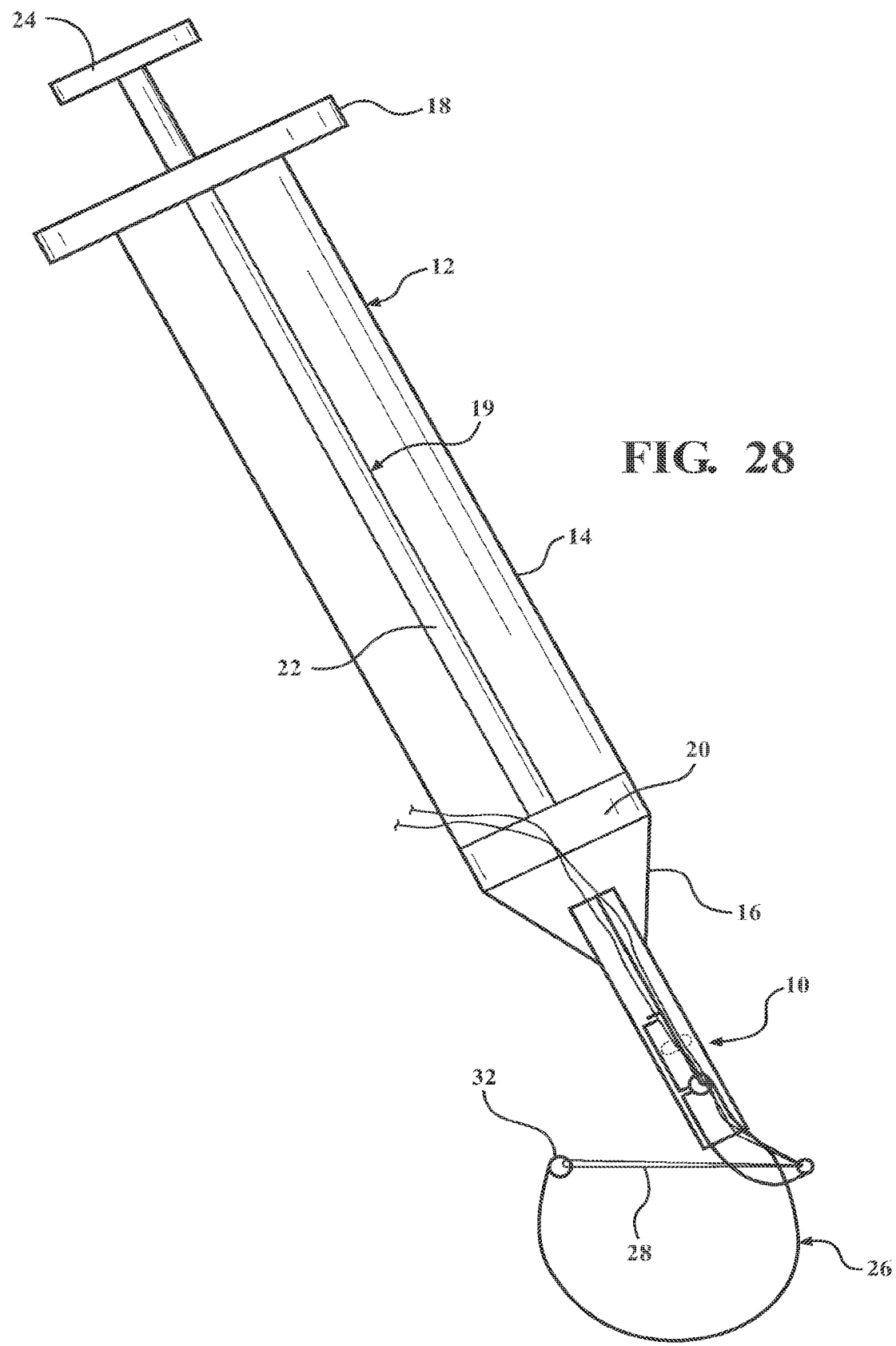
FIG. 28 is a perspective view of the CTR inserter of FIG. 24 illustrated in operational relationship with a syringe and a suture in a fully deployed state.
Figure 29:
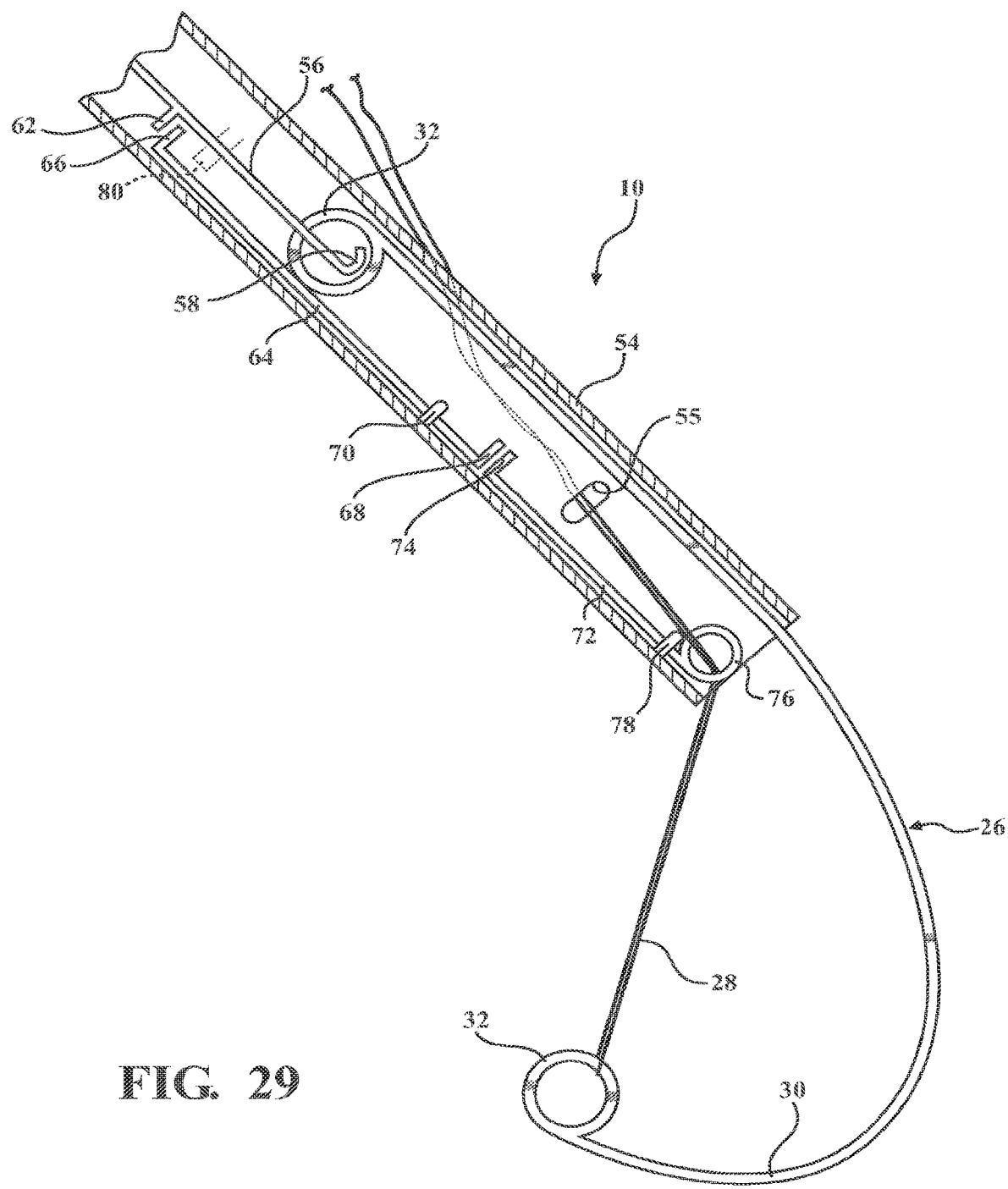
FIG. 29 is a fragmentary perspective view of a portion of the CTR inserter of FIG. 28 illustrated with the suture in a partially deployed state.

Referring to FIGS. 1 and 28, one embodiment of a capsular tension ring (CTR) inserter, according to the present invention and generally shown at 10, is illustrated in operational relationship with a syringe, generally indicated at 12. The syringe 12 includes a housing 14. The housing 14 is a generally hollow cylinder with a generally circular cross-sectional shape. The syringe 12 includes a nose 16 at a distal end of the housing 14 that couples to the CTR inserter 10 and a flange 18 that extends radially outwardly at a proximal end of the housing 14. The syringe 12 further includes an actuator or plunger mechanism, generally indicated at 19, cooperating with the CTR inserter 10. In one embodiment, the actuator 19 includes a movable internal piston 20 disposed within the housing 14, a piston rod 22 having one end connected to the piston 20 and extending axially through the flange 18 to another end, and an actuator member 24 connected to the other end of the piston rod 22 and extending radially. It should be appreciated that a user grasps the housing 14 and actuator 19 to manipulate a CTR 26 and a suture 28 to be described.

Figure 3:
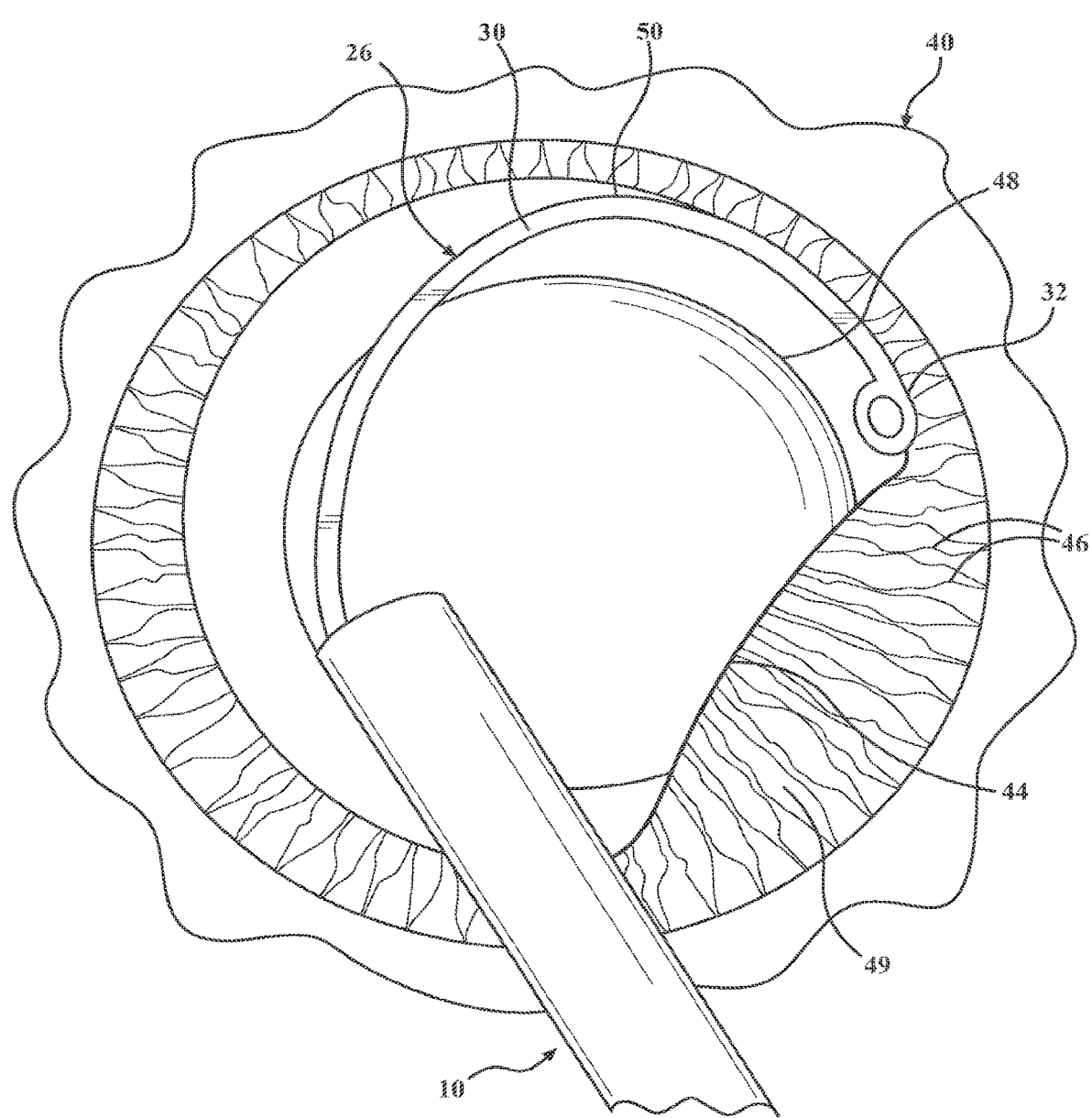
FIG. 3 is a view similar to FIG. 2 of the capsular tension ring entangled with the capsular bag and causing stresses on zonular fibers.
Figure 4:
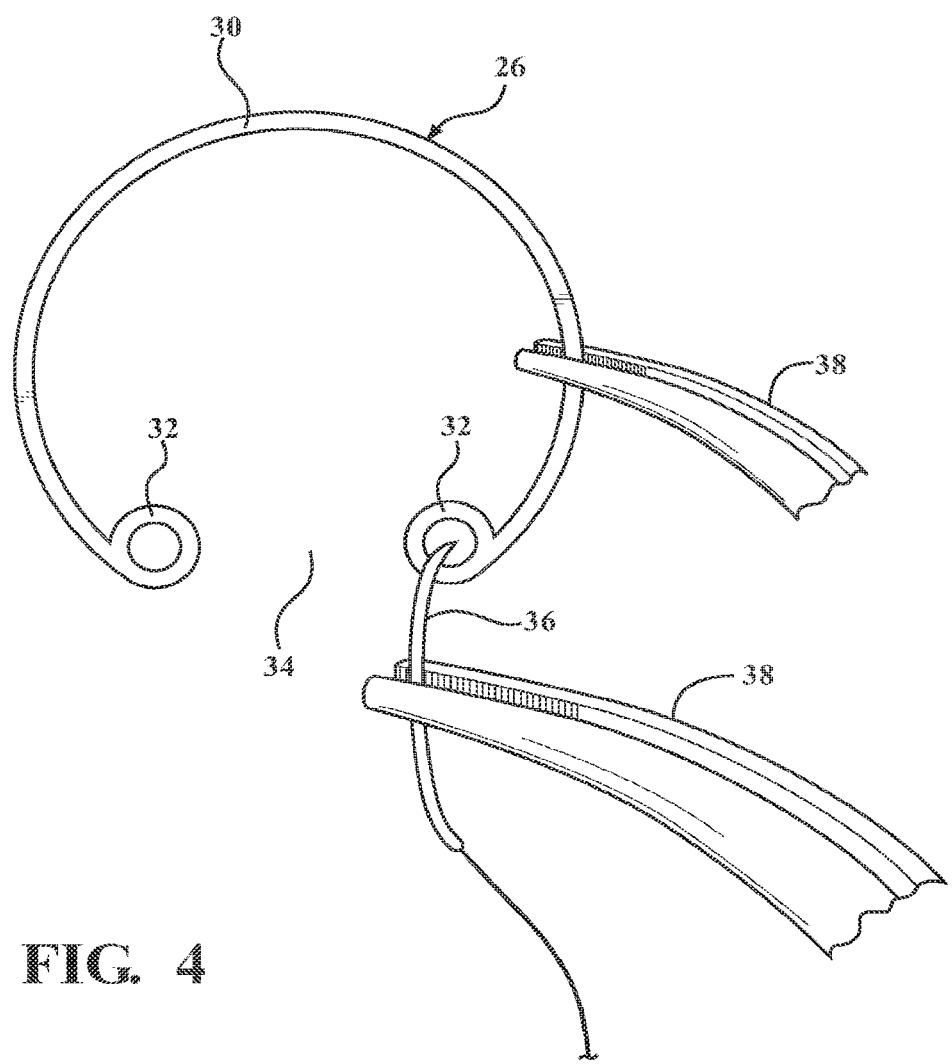
FIG. 4 is a schematic view of the capsular tension ring of FIGS. 2 and 3 with a suture being placed through a leading eyelet of a CTR.

Referring to FIG. 4, the CTR 26 is a poly(methyl methacrylate) ring approximately 0.2 mm thick with varying diameters. The CTR 26 has a body 30 that is horse-shoe shaped with a positioning eyelet 32 on at least one side, and preferably both sides of a gap 34. The eyelets 32 allow the body 30 to be placed into position with the CTR inserter 10 or a surgical hook instrument. The eyelets 32 are large enough to easily pass a 10-0 suture 28 (as shown in FIG. 3). After the suture 28 is passed through the eyelet 32, a needle 36 to guide the suture 28 may be cut off; however, the suture 28 should be kept long. It should be appreciated that forceps 38 may be used to grasp the CTR 26 and needle 36.

Figure 2:
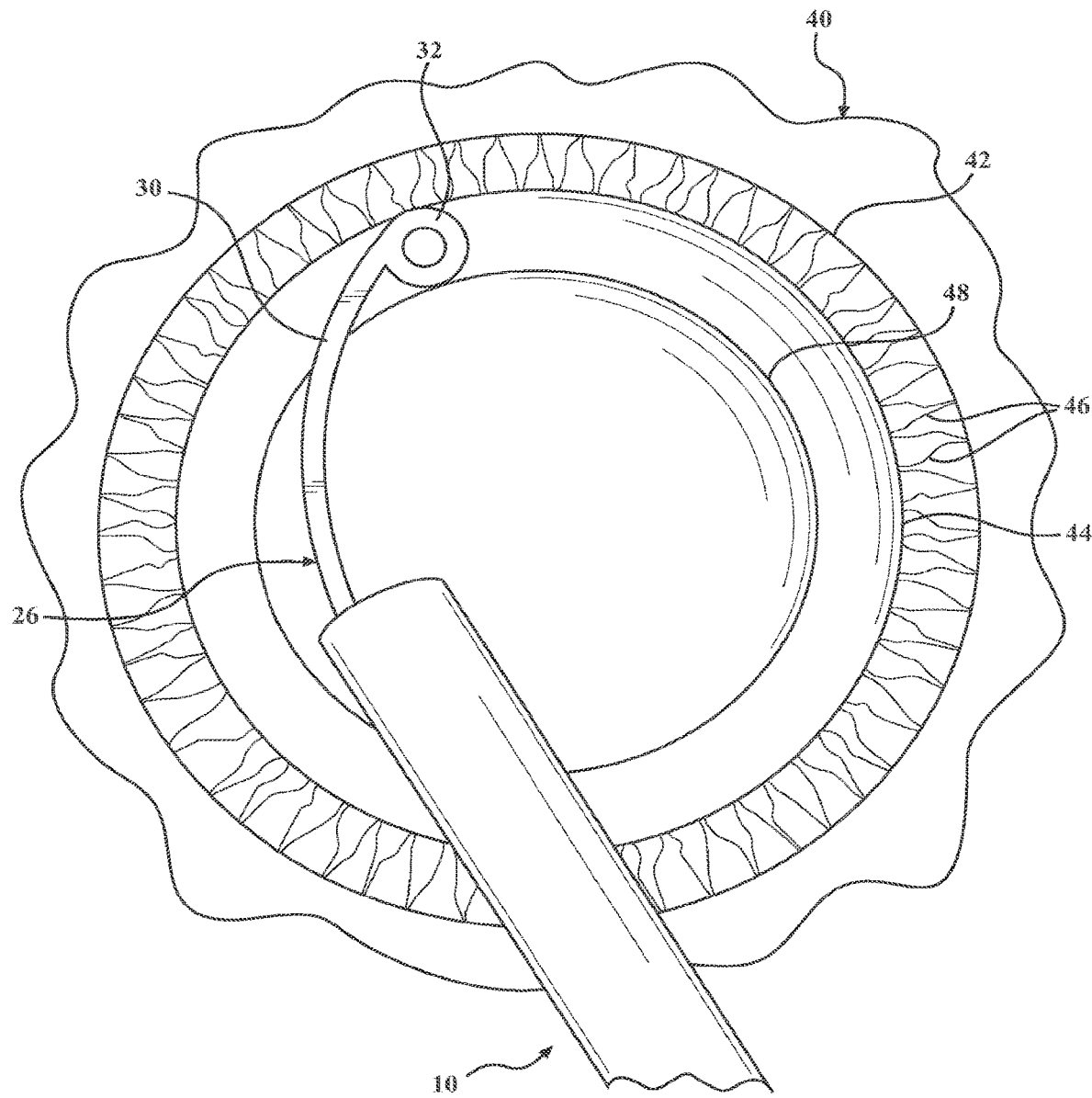
FIG. 2 is a schematic view of the CTR inserter of FIG. 1 with a capsular tension ring partially deployed within a capsular bag.

Referring to FIGS. 2 and 3, an eye, generally indicated at 40, is illustrated with the CTR inserter 10 and the CTR 26. The eye 40 includes a capsular bag 42 having an equator 44 and a plurality of zonular fibers or zonules 46 extending between the equator 44 and an outer periphery of the capsular bag 42. The eye 40 also includes a continuous curvilinear capsulorhexis (CCC) 48. It should be appreciated that an iris of the eye 40 has been omitted for illustrative purposes.

As illustrated, the CTR 26 creates tension within the capsular bag 42 to support an area of zonular weakness via recruitment of the surrounding intact zonular fibers or zonules 46. The CTR 26 is referred to as having 2 diameters, one in the open and the other in the compressed state. For example, the CTR 26 used for normal to myopic eyes has an open diameter of 13.0 mm and a compressed diameter of 11.0 mm. Because the diameter of the open CTR 26 is greater than the diameter of the capsular bag 42, tension will occur across the capsular bag 42 recruiting the strength of the intact zonular fibers or zonules 46. It should be appreciated that the CTR 26 automatically expands as it enters the fornix of the capsular bag 42 to its largest possible diameter based on its size and spring constant.

As illustrated in FIG. 3, complications may occur as the CTR 26 is inserted into the capsular bag 42 as torque is created at the point of contact between the CTR 26 and the capsular bag 42, potentially resulting in extension of a zonular dialysis or creating an iatrogenic dialysis 49. This tension creates an abnormal bend 50 in the CTR 26 with torque applied to the capsular bag 42 and the leading eyelet 32 of the CTR 26 is entangled in the capsular bag 42. The capsular bag 42 is displaced towards the point of torque contact. Stress on the zonules 46 is approximately 180 degrees away from the point of bag contact as the CTR 26 is deployed. As illustrated, the equator 44 of the capsular bag 42 is in the area of zonular dialysis, resulting in compromised zonules 46. It should be appreciated that CTR insertion has been proven to produce zonular stress and elongation with capsular bag displacement ranging from 0.5 mm to 4.0 mm depending upon the timing of insertion of the CTR 26.

The present invention includes a technique or method of using a suture 28 to mitigate the potential complications that may occur during CTR insertion as the CTR 26 is inserted into the capsular bag 42 of the eye 40. This is the first description of a suture-guided CTR insertion that maintains the intended shape and direction of implantation. This technique allows for precise control of the leading eyelet 32, thereby reducing the risk of capsular entanglement and iatrogenic zonular dialysis 49.

Figure 5:
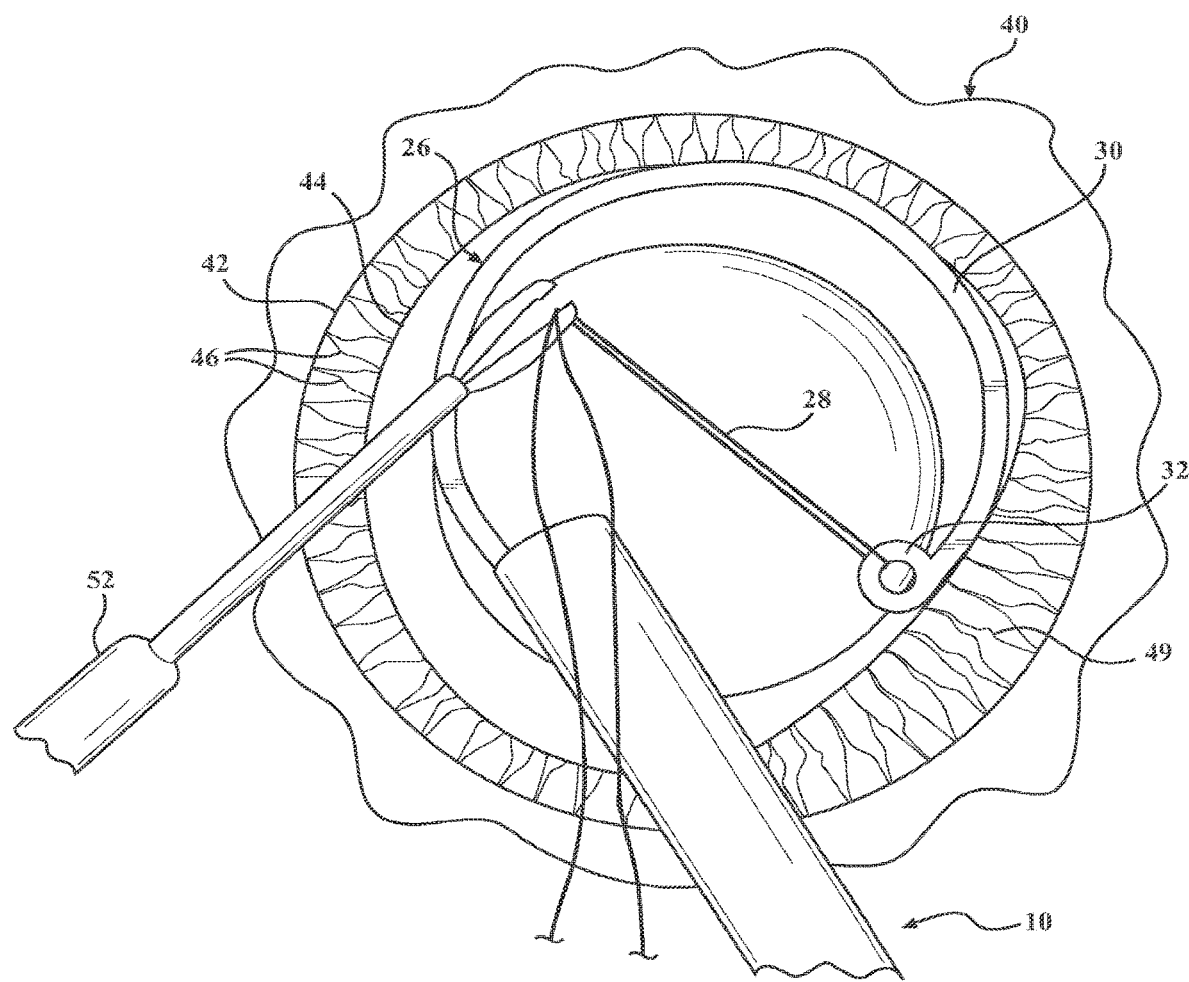
FIG. 5 is a schematic view of the capsular tension ring of FIG. 4 deployed by the CTR inserter within the capsular bag with an end of the capsular tension ring being guided by a suture and microforceps.

After adequate filling of the capsular bag 42 with an ophthalmic viscoelastic device (OVD), the leading eyelet 32 of the CTR with the suture 28 is introduced into the capsular bag 42 as illustrated in FIG. 5. As the CTR 26 is inserted into the capsular bag 42, gentle traction may be applied on the suture 28 with microforceps 52 to guide the leading eyelet 32 centrally mitigating the risk of extending a dialysis or creating iatrogenic dialysis. The surgeon may use visual cues of CTR entanglement and subsequent capsular bag displacement by observing the position of the capsulorhexis while inserting the CTR 26. If displacement is suspected, the microforceps 52 may be used to pull the leading eyelet 32 of the CTR 26 away from areas of torque to ease the stress on the zonular fibers 46 as illustrated in FIG. 5.

The same maneuver may be applied if the dialysis appears to be extending during the insertion of the CTR 26. Typically the extension of the dialysis or creation of an iatrogenic dialysis 49 will occur approximately 180 degrees away from the area of torque applied by the advancing CTR to the fornix of the capsular bag 42. The microforceps 52 and suture-guided CTR 26 gives the surgeon control within the eye 40 to achieve different angles of tension to guide the CTR 26 during insertion. If the proper angle cannot be achieved, a second. paracentesis may be made for the microforceps 52.

After the CTR 26 has been safely and fully deployed, the suture 28 will remain in the leading eyelet 32 of the CTR 26 as it comes to rest in the fornix of the capsular bag 42. The suture 28 can be cut at the incision and simply pulled on one end to remove it from the eyelet 32.

The suture-guided CTR insertion enables the surgeon to achieve more precise control of the CTR 26 as it passes through vulnerable areas of compromised zonular fibers or zonules 46. Modifications have been made to the shape of the standard CTR 26 to help reduce capsular entrapment of the leading eyelet 32 of the CTR 26. Although such a modification may help reduce iatrogenic damage due CTR entrapment or capsule entanglement of the leading eyelet 32, this modification would not necessarily mitigate torque force as arc of the CTR 26 makes contact with the fornix of the capsular bag 42. It should be appreciated that, the suture guided CTR technique described herein, is a method to control and minimize both leading eyelet entrapment and torque forces applied to the capsular bag 42 that also serves as a position indicator for the leading eyelet 32 of the CTR 26.

Referring to FIGS. 6-11 and 24-30, other embodiments, according to the present invention, of the CTR inserter 10 is shown. In this embodiment, the CTR inserter 10 includes an inserter tube or cannula 54 coupled to the nose of the syringe 12. The cannula 54 is a generally hollow cylinder having a generally circular cross sectional shape. The cannula 54 may include an opening 55 that allows externalization of the suture 28 for control by the surgeon.

The CTR inserter 10 also includes hook element 56 slideably disposed in the cannula 54 and extending axially with a hook end 58 engaging a trailing eyelet 32 of the CTR 26 and a connecting end (not shown) connected to the piston 20 of the syringe 12. The hook element 56 also has an appendage 62 disposed between the hook end 58 and connecting end and extending radially to move a piston 64 to be described. The hook element 56 is anchored to the cannula 54 by an anchoring element 57 that allows sliding movement of the hook element 56.

The CTR inserter 10 further includes a piston 64 slideably mounted in the cannula 54. The piston 64 extends axially and has a first end 66 and a second end 68. The piston 64 is anchored to the cannula 54 by an anchoring element 70 that allows sliding movement of the piston 64. It should be appreciated that the first end 66 of the piston 64 contacts the appendage 62 and the second end 68 of the piston 64 connects a guide element 72 to be described.

The CTR inserter 10 includes a guide element 72 slideably disposed and mounted in the cannula 54. The guide element 72 extends axially and has a piston end 74 to contact the piston 64 and an eyelet end 76 at the other end for the suture 28. The guide element 72 is anchored to the cannula 54 by an anchoring element 78 that allows sliding movement of the guide element 72. It should be appreciated that the piston end 74 of the guide element 72 contacts the second end 68 of the piston 64 and the eyelet end 76 connects to the suture 28. It should also be appreciated that the guide element 72 is attached by way of the suture 28 to the CTR 26. It should also be appreciated that the suture 28 can be pre-placed through the leading eyelet 32 of the CTR 26, through the eyelet end 76 of the guiding element 72 and externalized through the opening 55 of the cannula 54 of the CTR inserter 10 prior to use. It should further be appreciated that the opening 55 could also be omitted with the trailing suture 28 contained within the cannula 54. It should still further be appreciated that the CTR inserter 10 may include a clip 80 disposed on the cannula 54 having a low profile to secure the suture 28 in the cannula 54.

In operation, the appendage 62 of the hook element 56 engages and moves the piston 64 during deployment. The piston 64 in turn engages and actuates the guide element 72 during deployment of the CTR 26. Once the CTR 26 is safely in the capsular bag 42, the hook element 56 is lifted out of the trailing eyelet 32 of the CTR 26. Once deployed, the suture 28 is then cut and removed from the eyelet 32. The suture 28 also serves as a safety mechanism in the event that the CTR 26 becomes dislodged into the posterior segment of the eye 40, allowing simple retrieval by the trailing end of the suture 28.

As the CTR 26 is deployed through the CTR inserter 10, the surgeon will he able to mitigate torque forces applied to the fornix of the capsular bag 42 to help prevent iatrogenic zonular damage and vitreous loss with ensuing complications. The surgeon is able to control the deployment of the CTR 26 through the actuator 19 (see FIG. 28), however, the CTR inserter 10 of the present invention offers two additional methods of control. First, the externalized suture 28 allows the surgeon to apply tension to a leading eyelet 32 of the CTR 26 if any capsular bag displacement is recognized by the surgeon. The opening 55 in the CTR inserter 26 is provided to allow access to the suture 28 for control by the surgeon. Tension applied by the surgeon to the leading eyelet 32 is likely to alleviate unwanted torque to the capsular bag 42. Secondly, the guide element 72 extends from the CTR inserter 10 in an opposite direction of the CTR 26 to mitigate the tension forces of the leading eyelet 32 of the CTR 26 against the capsular bag 42. As the CTR 26 is deployed the guide element 72 will follow at a pre-determined interval based upon a set distance between the piston element 64 and the guide element 72. As the guide element 72 deploys it will provide counter traction approximately 180° away from the point of contact of the CTR 26 in the capsular bag 42 where the greatest risk of capsular bag torque occurs, mitigating those forces and reducing risk of iatrogenic damage to the zonules 46 of the eye 40.

Figure 30:
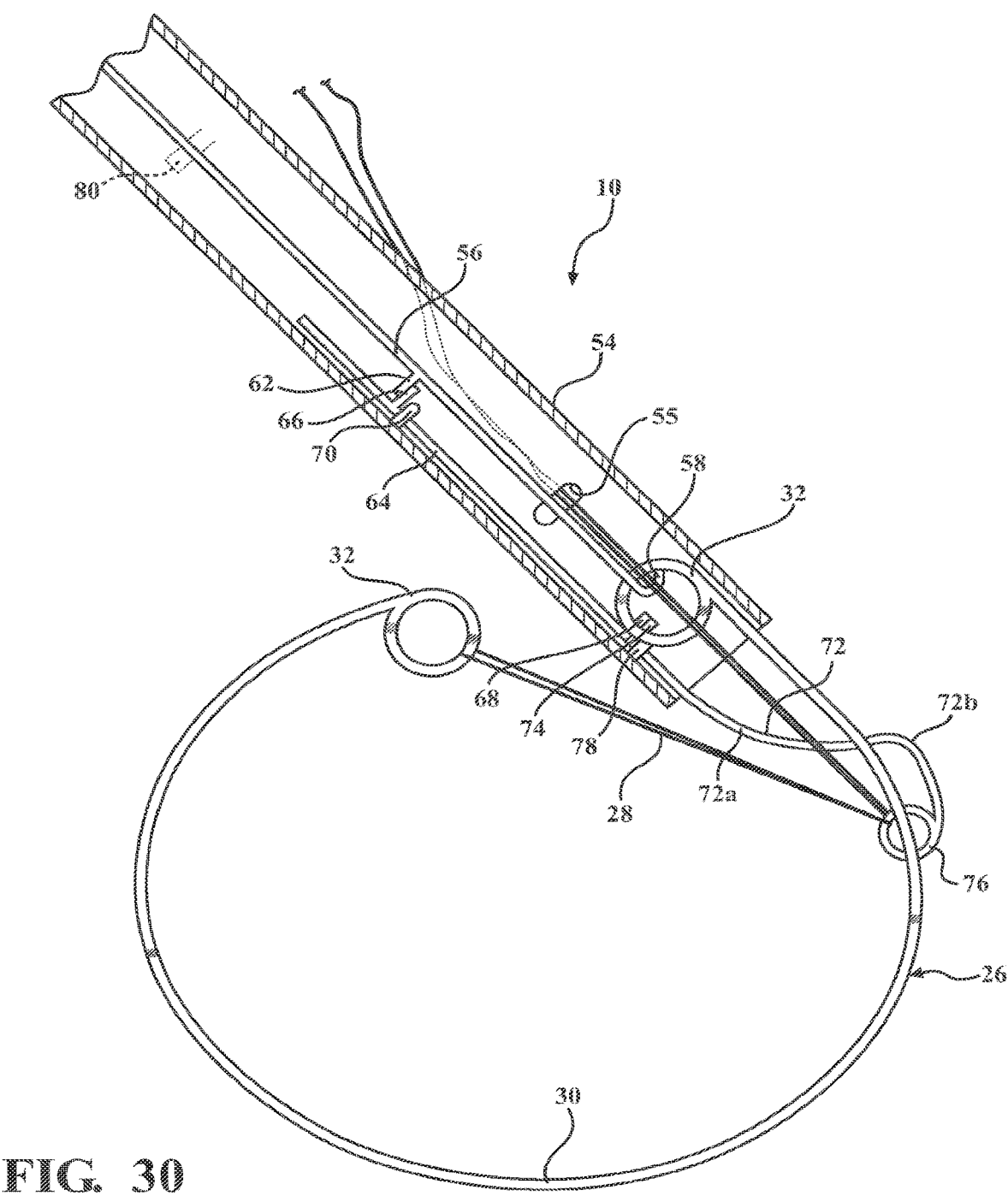
FIG. 30 is a fragmentary perspective view of a portion of the CTR inserter of FIG. 28 illustrated with the suture in an almost fully deployed state.

As illustrated in FIG. 30, another embodiment, according to the present invention, of the CTR inserter 10 is shown. In this embodiment, the CTR inserter 10 continues to include the piston 64 and the guide element 72. When the guide element 72 is deployed, the guide element 72 has a first portion 72a that arcs away from the CTR 26 and a second portion 72b that extends from the first portion 72a. The second portion 72b includes the eyelet end 76 mounted to the end thereof. It should be appreciated that the actuator 19 of FIG. 28 is similar to the mechanism of other embodiments. It should also be appreciated that, as the guide element 72 deploys, it will provide counter traction away from the point of contact of the CTR 26 in the capsular bag 42 where the greatest risk of capsular bag torque occurs, mitigating those forces and reducing risk of iatrogenic damage to the zonules 46 of the eye 40.

Figure 31:
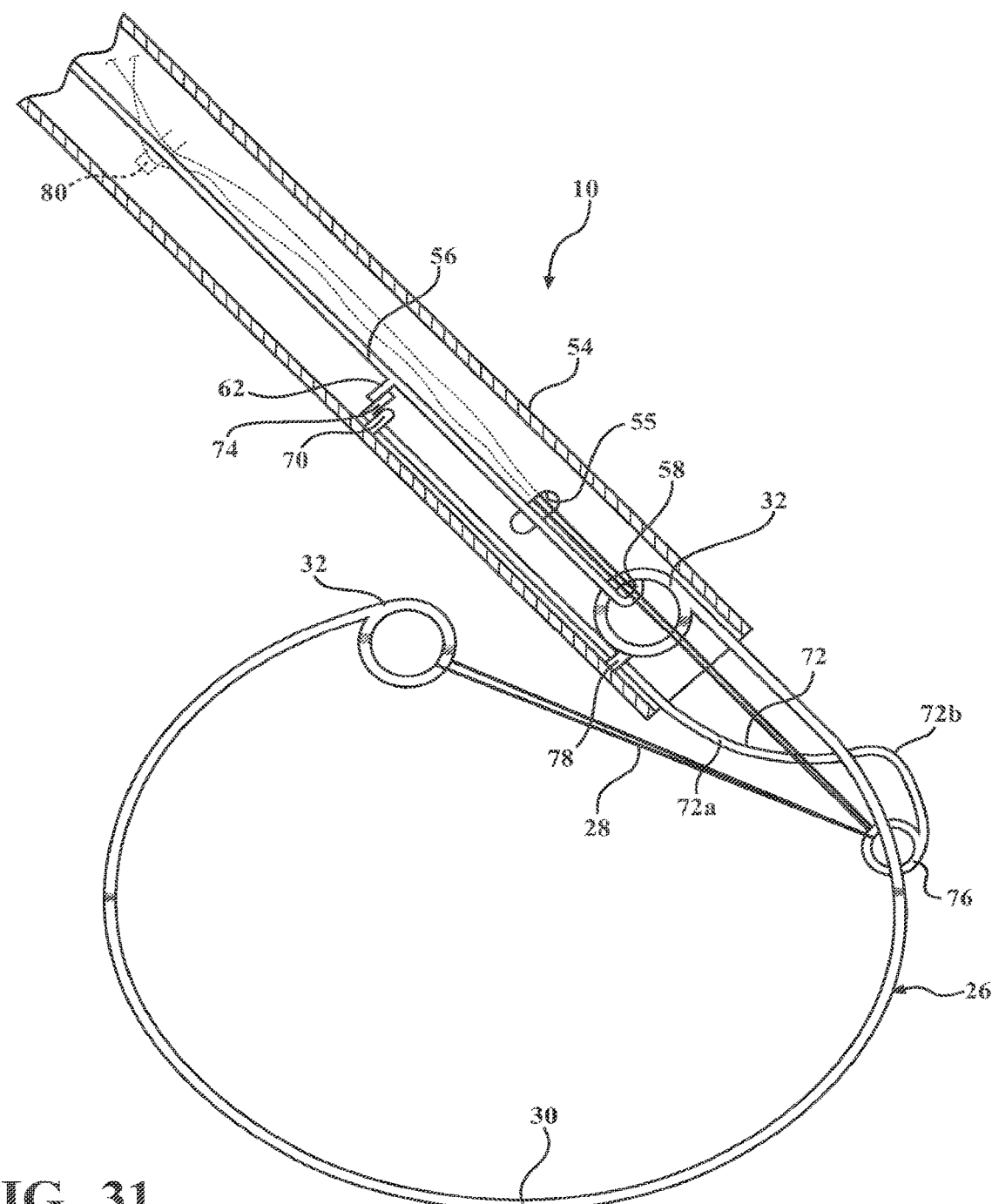
FIG. 31 is still a further embodiment, according to the present invention, of the CTR inserter of FIG. 28 without a piston illustrated with the suture in an almost fully deployed state.

Turning now to FIG. 31, another embodiment, according to the present invention, of the CTR inserter 10 is shown. In this embodiment, the CTR inserter 10 eliminates the piston 64 and reconfigures the guide element 72. The guide element 72 continues to be slideably mounted within the cannula 54 of the CTR inserter 10 and continues to be attached to the CTR 26 through the suture 28. The guide element 72 of FIG. 31 has a similar configuration to the guide element 72 of FIG. 30 with a first portion 72a arcing away from the CTR 26 and a second portion 72b extending from the first portion 72a. The second portion 72b also includes the eyelet 76 mounted to the end thereof. It should be appreciated that, the actuator 19 of FIG. 28 is also similar to the mechanism of other embodiments. It should also be appreciated that, as the guide element 72 deploys, it will provide counter traction away from the point of contact of the CTR 26 in the capsular bag 42 where the greatest risk of capsular bag torque occurs. It should further be appreciated that the hook element 56 has the appendage 62 that engages and moves the guide element 72 directly during deployment. It should still further be appreciated that, once the CTR 26 is safely in the capsular bag 42, the hook element 56 is lifted out of the trailing eyelet 32 of the CTR 26.

Referring to FIGS. 6, 6A, 7-11 and 14-23, the CTR inserter 10 may have at least one port 84 and may have a plurality of ports 84 disposed within a distal end of the CTR inserter 10. As illustrated in the various views of FIGS. 6, 6A, 7-11 and 14-23, the ports 84 can be disposed in different locations. Further, the cannula 54 of the CTR inserter 10 may have a notch 86 defining at least one flange 88 extending outwardly therefrom. The port 84 may be disposed within the flange 88. The flange 88 may be of any suitable configuration and there may be any number of flanges 88. In the specific embodiments shown, one of them has a singular port 84 and the other embodiment has two ports 84. The embodiment with the two ports 84 has the ports 84 disposed at substantially right angles to each other. Correspondingly, the flanges 88 are also disposed at right angles with each other.

Figure 22:
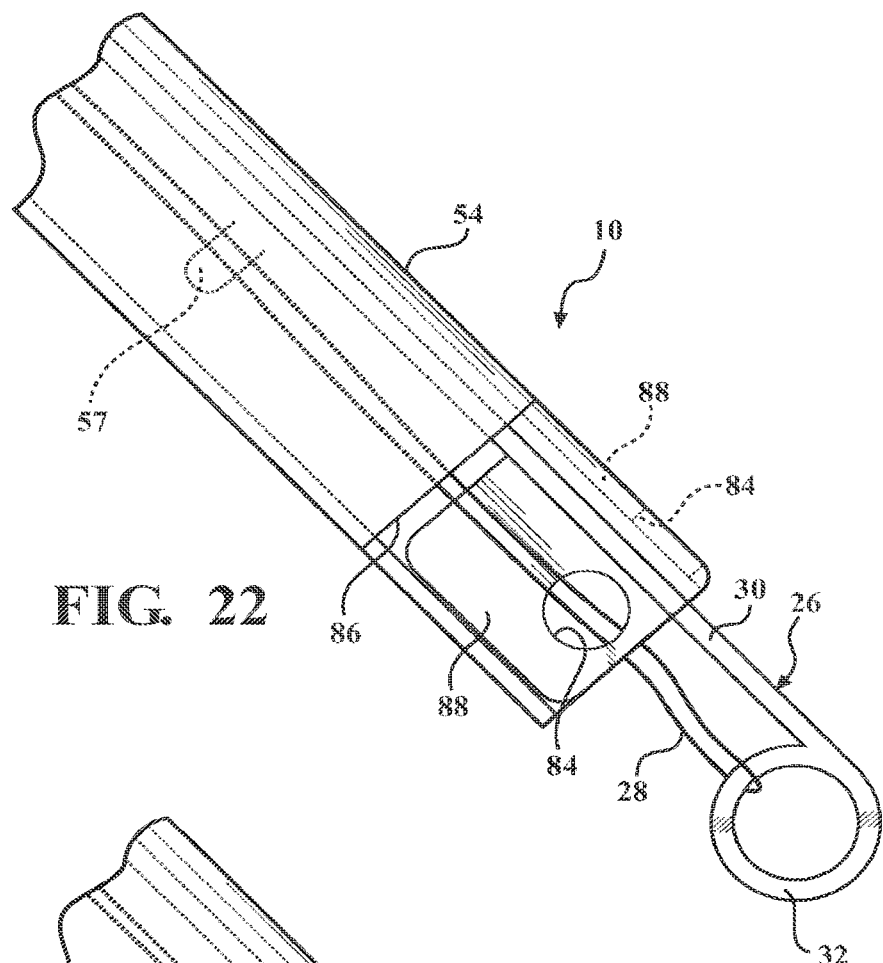
FIGS. 22 and 23 are schematic plan views of two embodiments of the CTR inserter, with the CTR inserter of FIG. 19 shown in a partially deployed state and also in a retracted/loaded state with the suture passed through the CTR and both the fist and second ends passed through the port.
Figure 23:
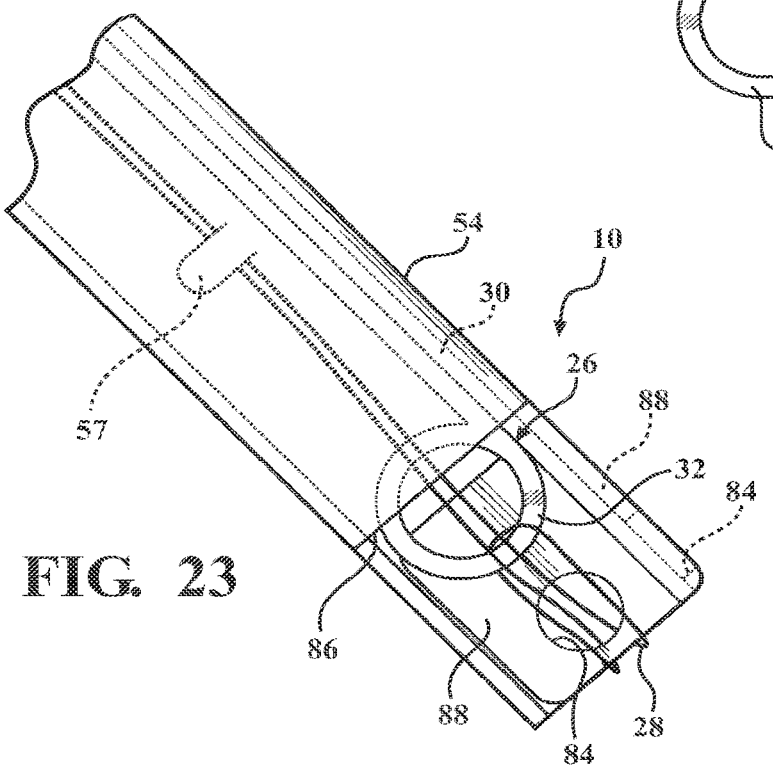
Figure 24:
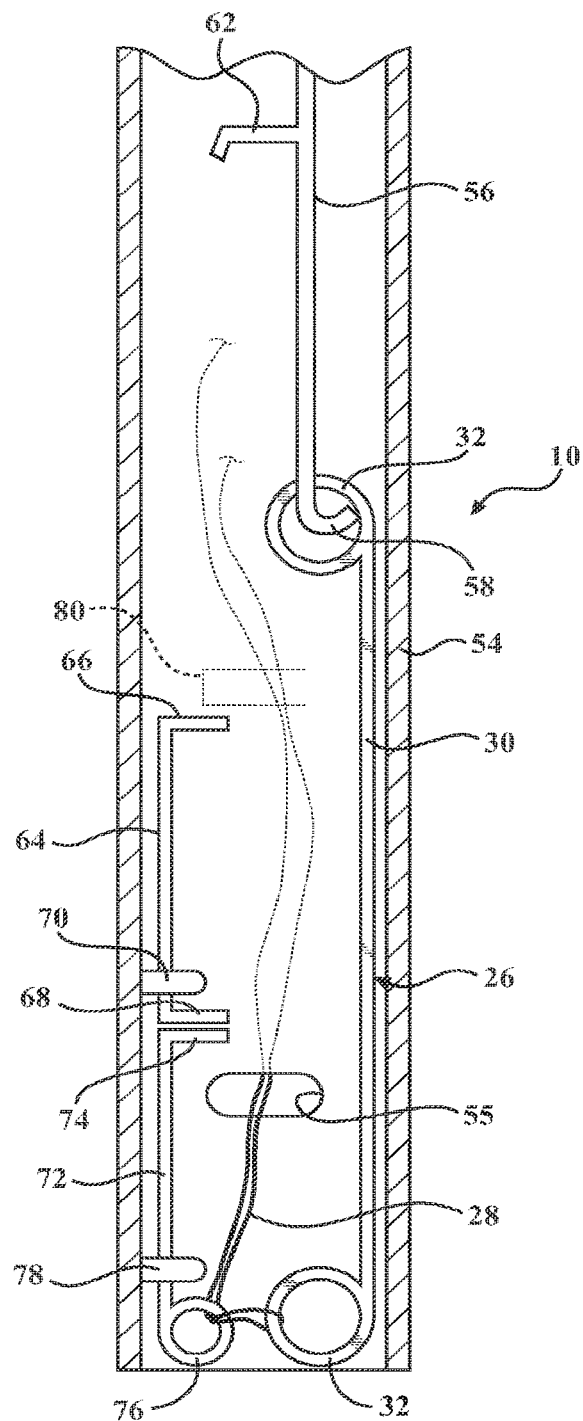
FIG. 24 is a fragmentary view of yet a further embodiment, according to the present invention, of the CTR inserter of FIG. 1 illustrated with a suture.
Figure 25:
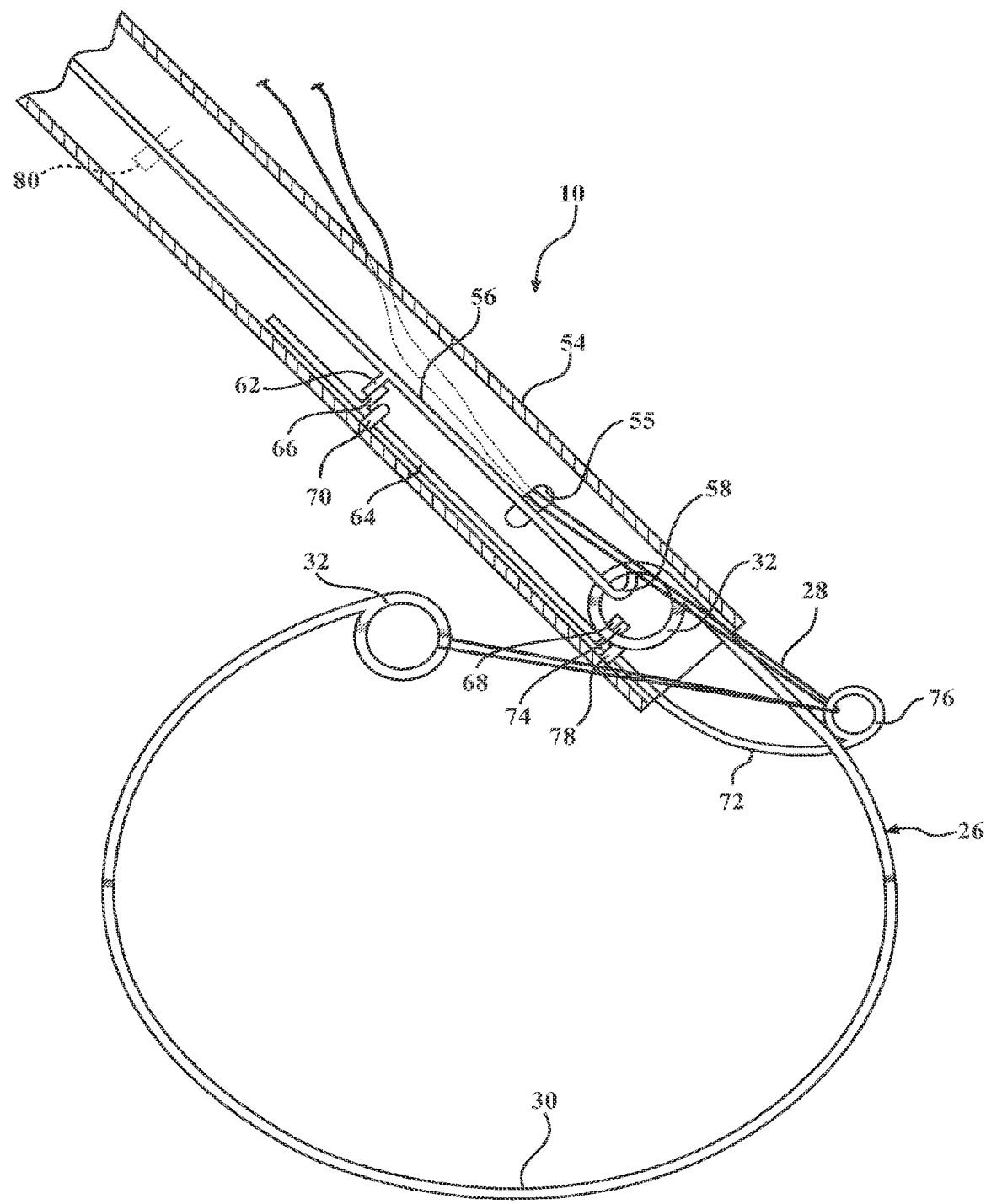
FIG. 25 is a fragmentary perspective view of the CTR inserter of FIG. 24 illustrated in a fully deployed state.
Figure 26:
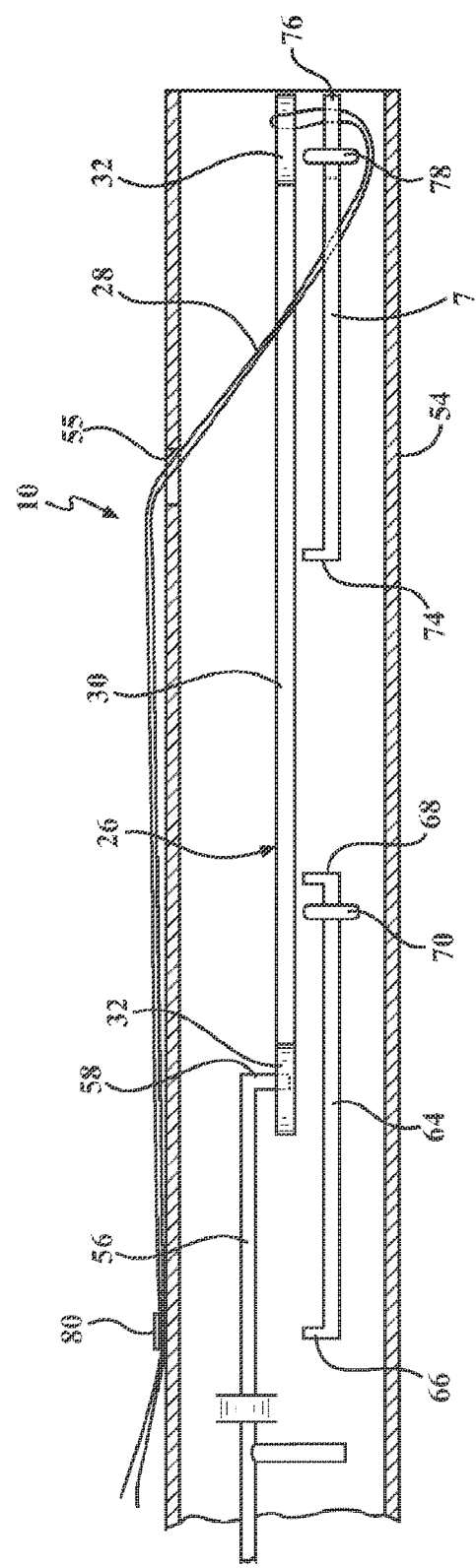
FIG. 26 is a fragmentary elevational view of the CTR inserter of FIG. 24.
Figure 27:
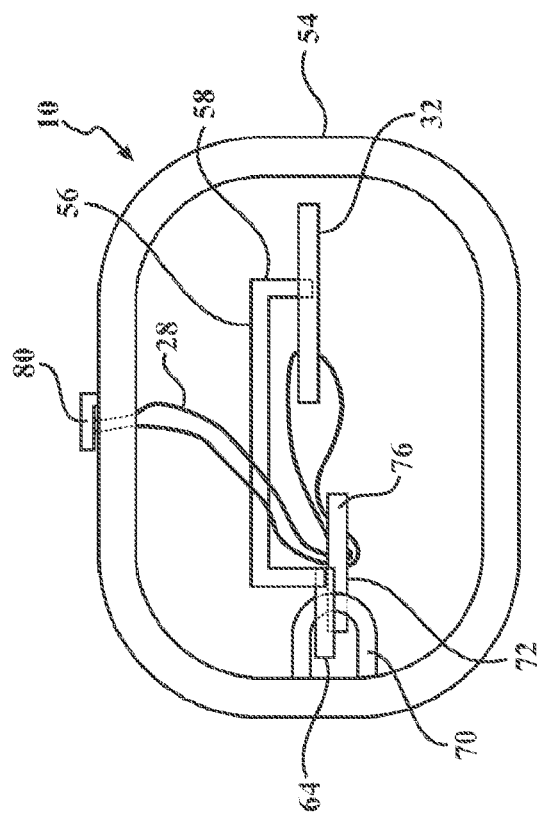
FIG. 27 is an elevational view of an open distal end of the CTR inserter of FIG. 24.

As shown in the progression of steps in FIGS. 7-11 and 19-23, the CTR 26 is moved to a partially deployed position. Preferably, this partially deployed position will be a relatively small amount of deployment of the CTR 26 from the CTR inserter 10. While partially deployed, a first end of a suture 28 is inserted through the leading eyelet 32 of the CTR 26 and then through the port 84 of the CTR inserter 10. The second end of the suture 28 is then passed through the port 84, preferably the same port 84, with the suture 28 remaining looped around the leading eyelet 32 of the CTR 26. A trailing portion of the second end of the suture 28 is then held in place by a suture hold on or inside the CTR inserter 10. As shown in FIGS. 22 and 23, a trailing portion of the first end of the suture 28 is subsequently held in place by the suture hold or clip 80. It is preferred that the installation of the suture 28 is performed prior to inserting the CTR inserter 10 into a patient. The CTR 26 is then retracted within the CTR inserter 10 to define a loaded position. The suture 28 remains looped around the leading eyelet 32 of the CTR 26 and the port 84 when in the loaded position.

Figure 6:
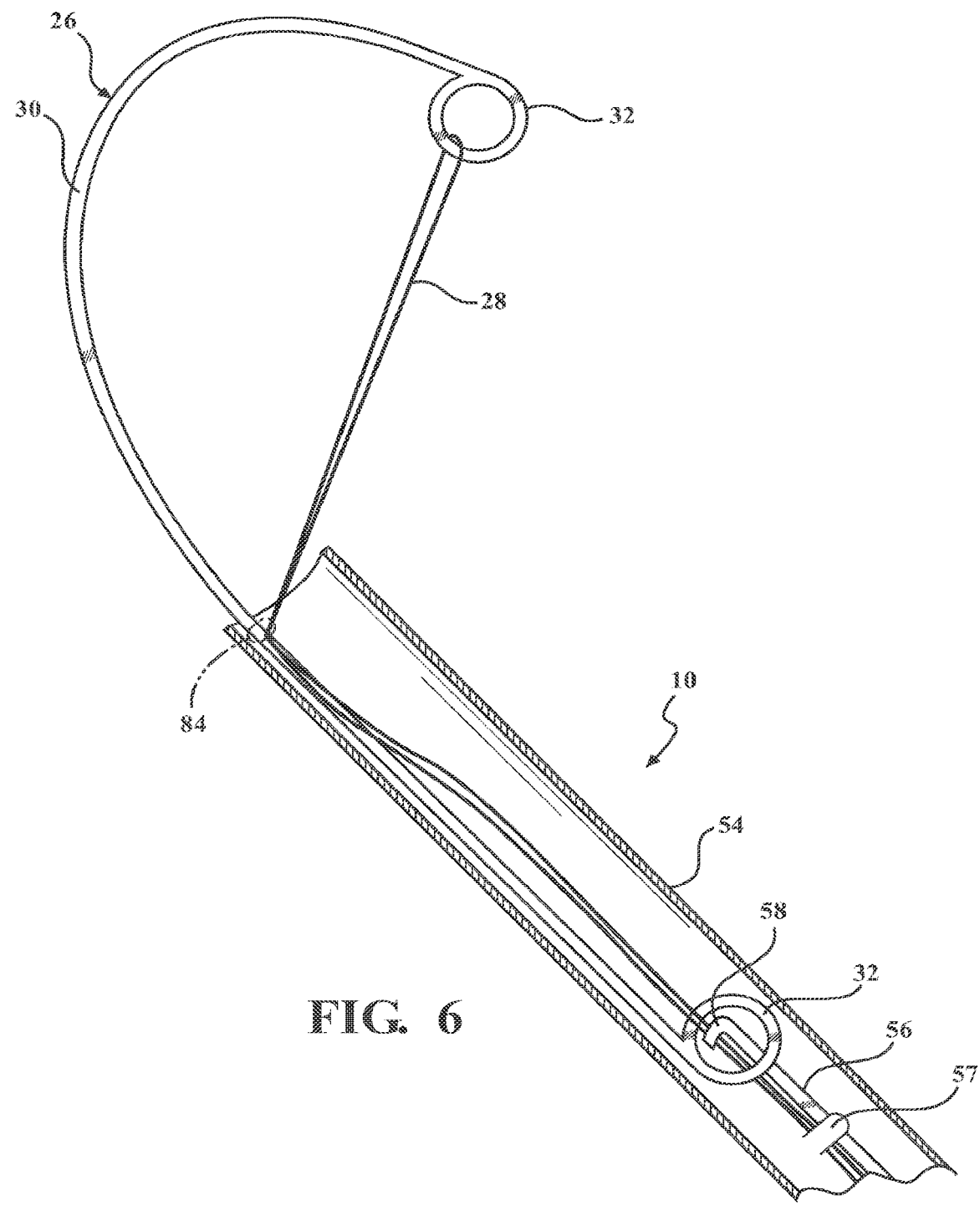
FIG. 6 is a fragmentary view of another embodiment, according to the present invention, of the CTR inserter of FIG. 1 illustrated in a retracted state.
Figure 6A:
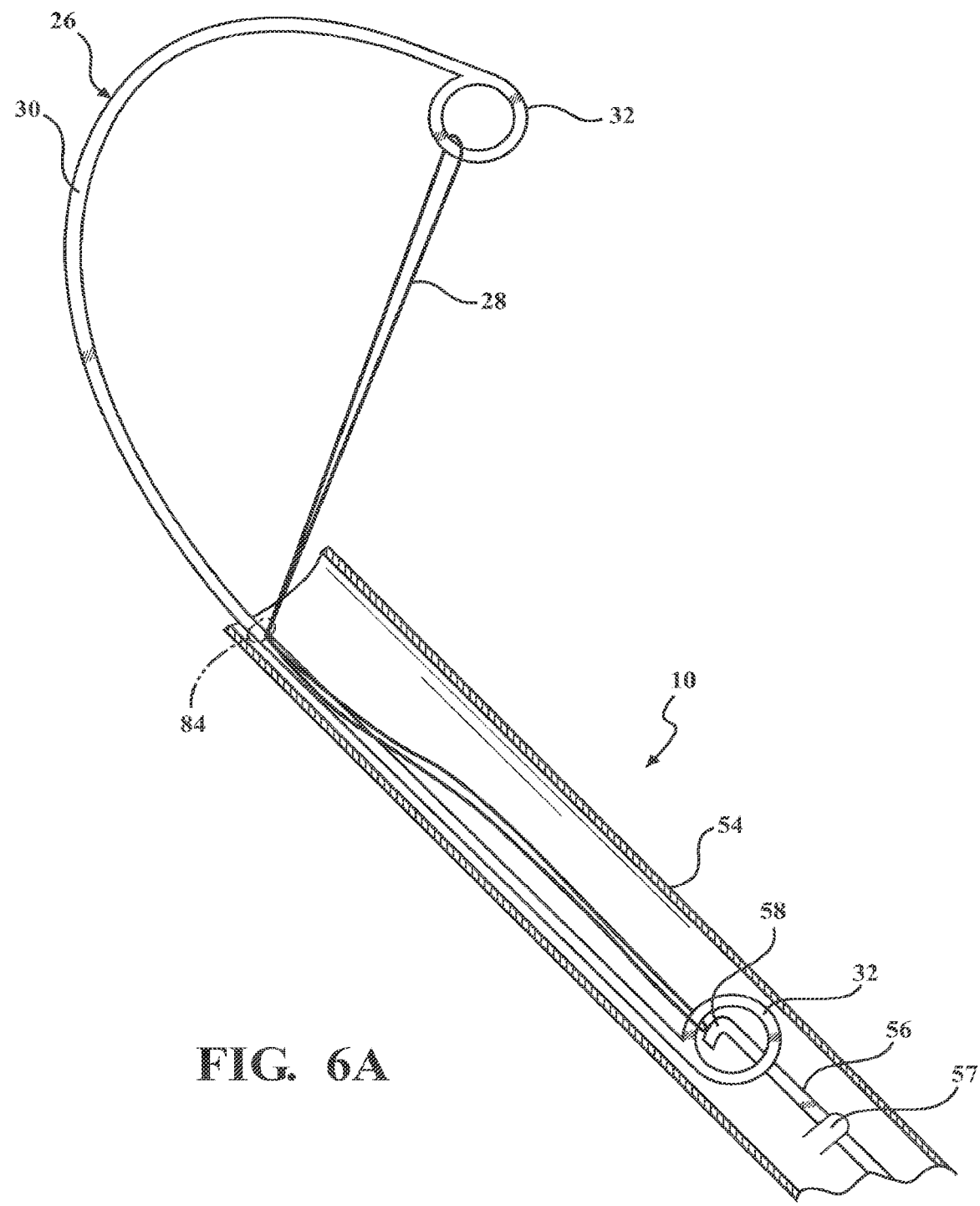
FIG. 6A is a fragmentary view of yet another embodiment, according to the present invention, of the CTR inserter of FIG. 1 illustrated in a retracted state.

As illustrated in FIG. 6A, in another embodiment, according to the present invention, of the CTR inserter 10 is shown. In this embodiment, the other end of the suture 28 is also hooked around the trailing eyelet 32 of the CTR 26. It is to be appreciated that the suture 28 can be pre-loaded or pre-placed through a leading eyelet 32 of the CTR 26 and externalized through the port 84 of the cannula 54 of the CTR inserter 10 prior to use. It should be appreciated that it is contemplated that the suture 28 would be installed within the CTR inserter 10 by the CTR inserter manufacturer as opposed to the surgeon.

Figure 6B:
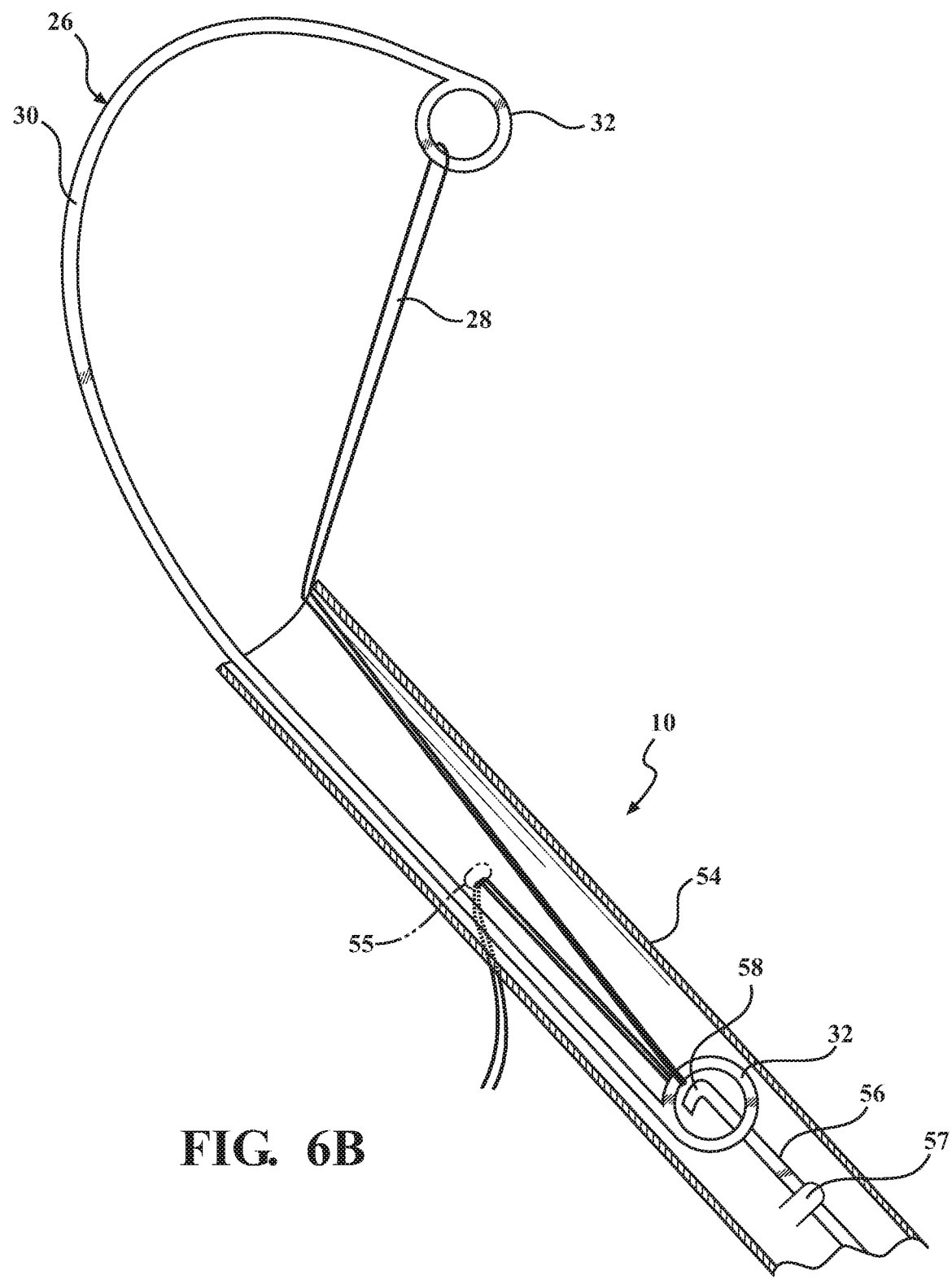
FIG. 6B is a fragmentary view of still another embodiment, according to the present invention, of the CTR inserter of FIG. 1 illustrated in a retracted state.
Figure 6C:
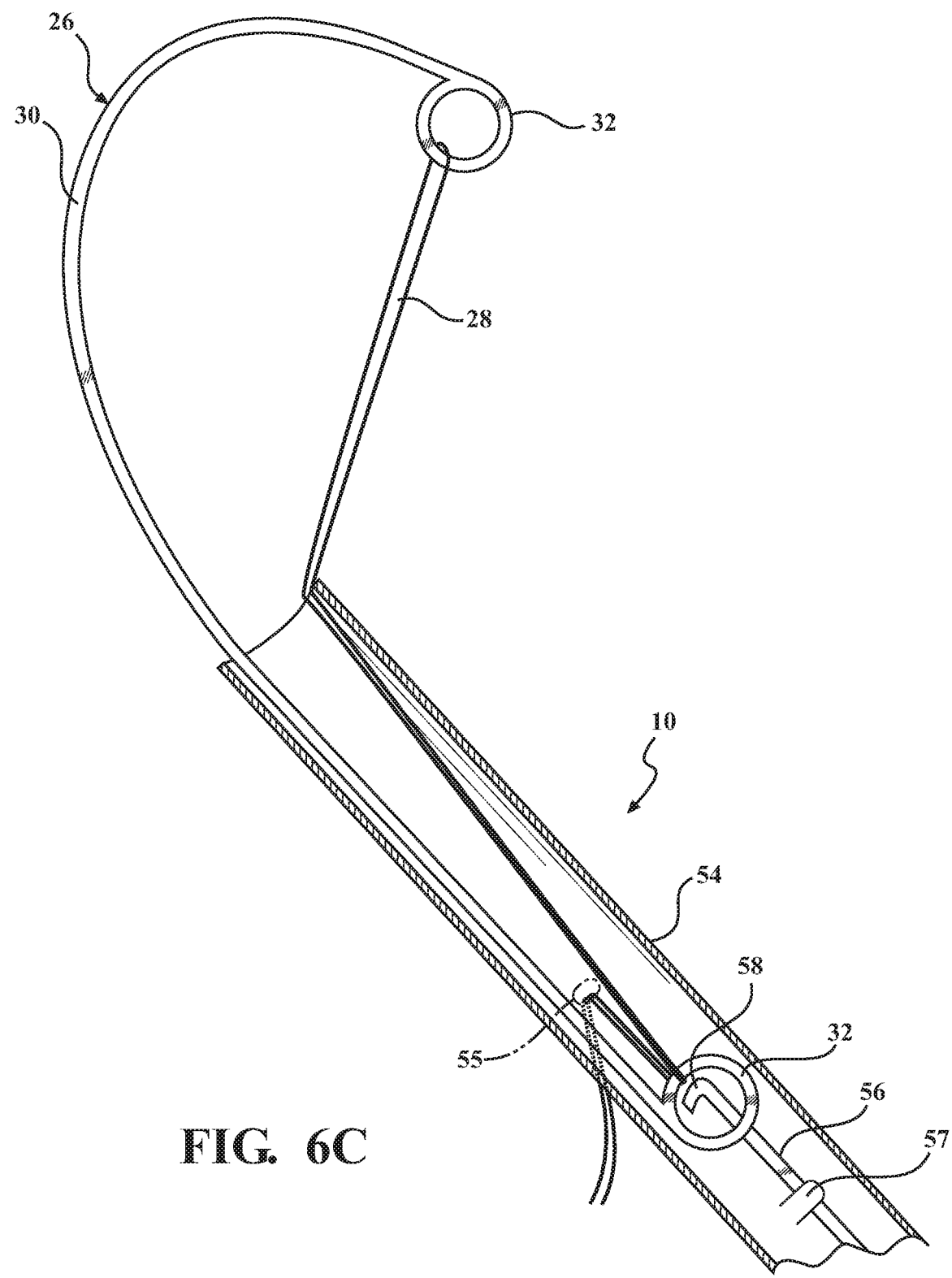
FIG. 6C is a fragmentary view of a further another embodiment, according to the present invention, of the CTR inserter of FIG. 1 illustrated in a retracted state.
Figure 7:
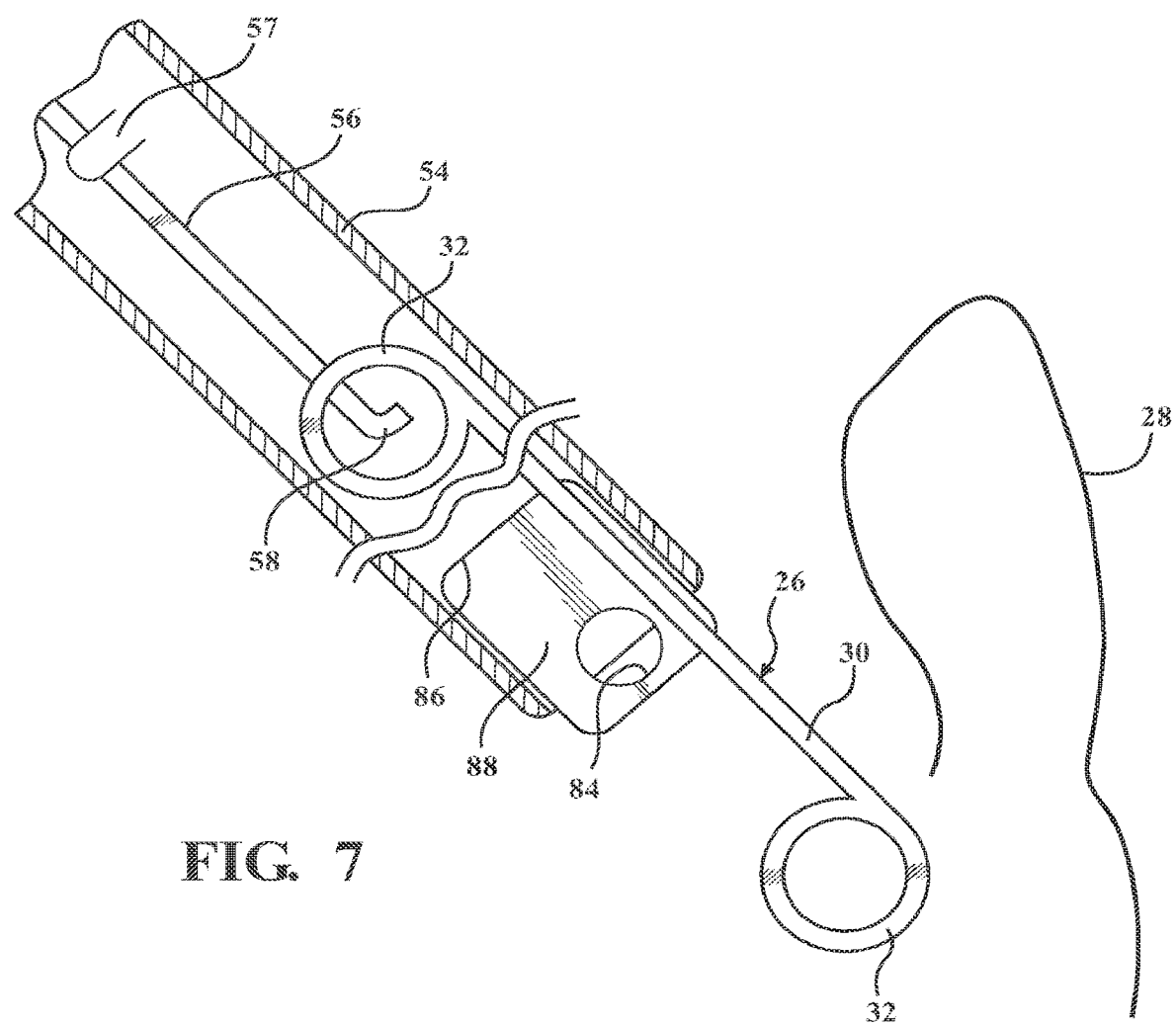
FIG. 7 is a fragmentary view of a still further embodiment, according to the present invention, of the CTR inserter of FIG. 1 illustrated in a deployed state.
Figure 8:
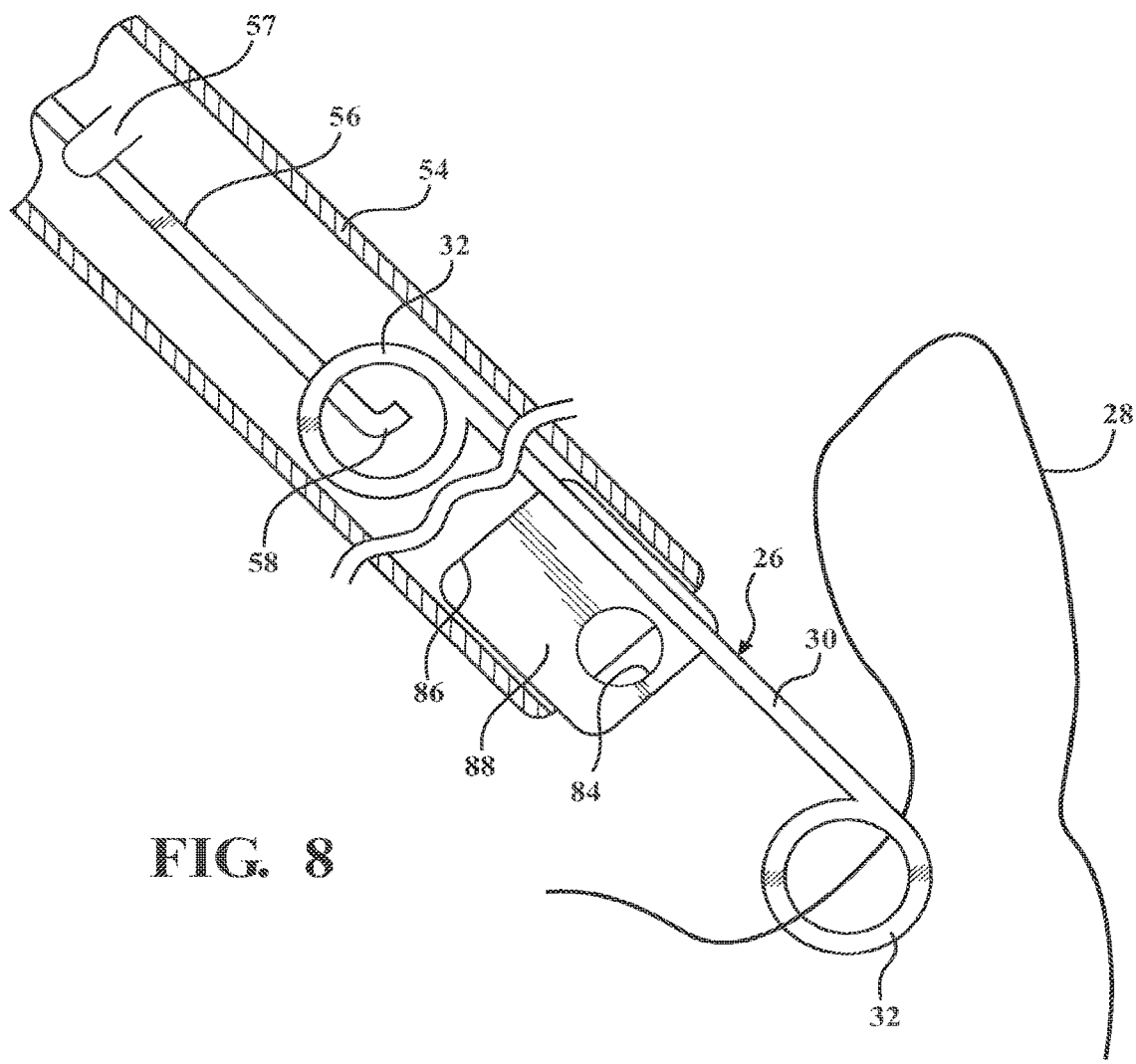
FIG. 8 is a fragmentary view of the CTR inserter of FIG. 7 illustrated in a first operative position.
Figure 9:
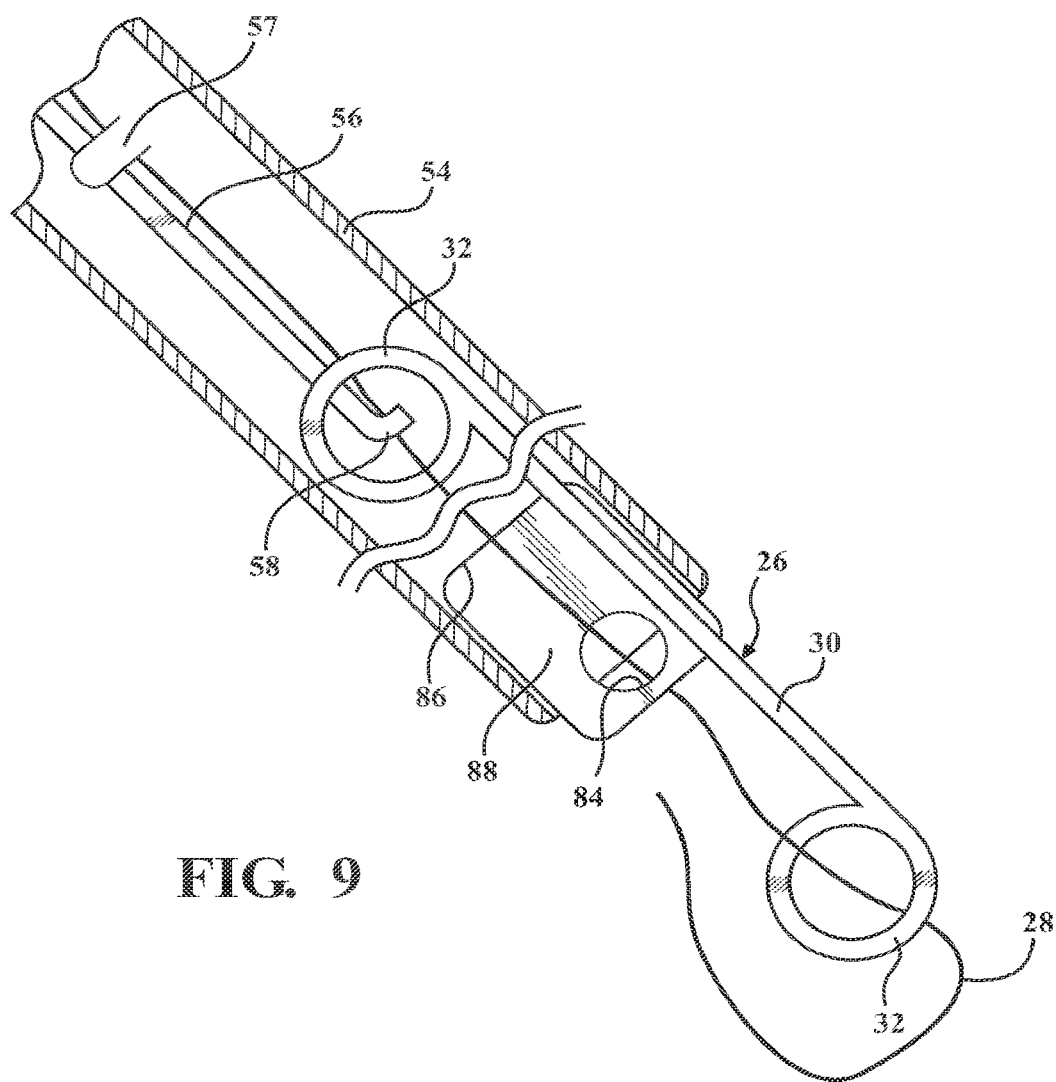
FIG. 9 is a fragmentary view of the CTR inserter of FIG. 7 illustrated in a second operative position.
Figure 10:
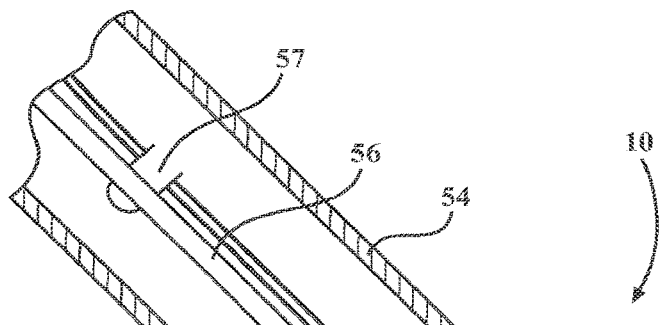
FIG. 10 is a fragmentary view of the CTR inserter of FIG. 7 illustrated and. connected to a plunger and in a partially deployed state.
Figure 11:
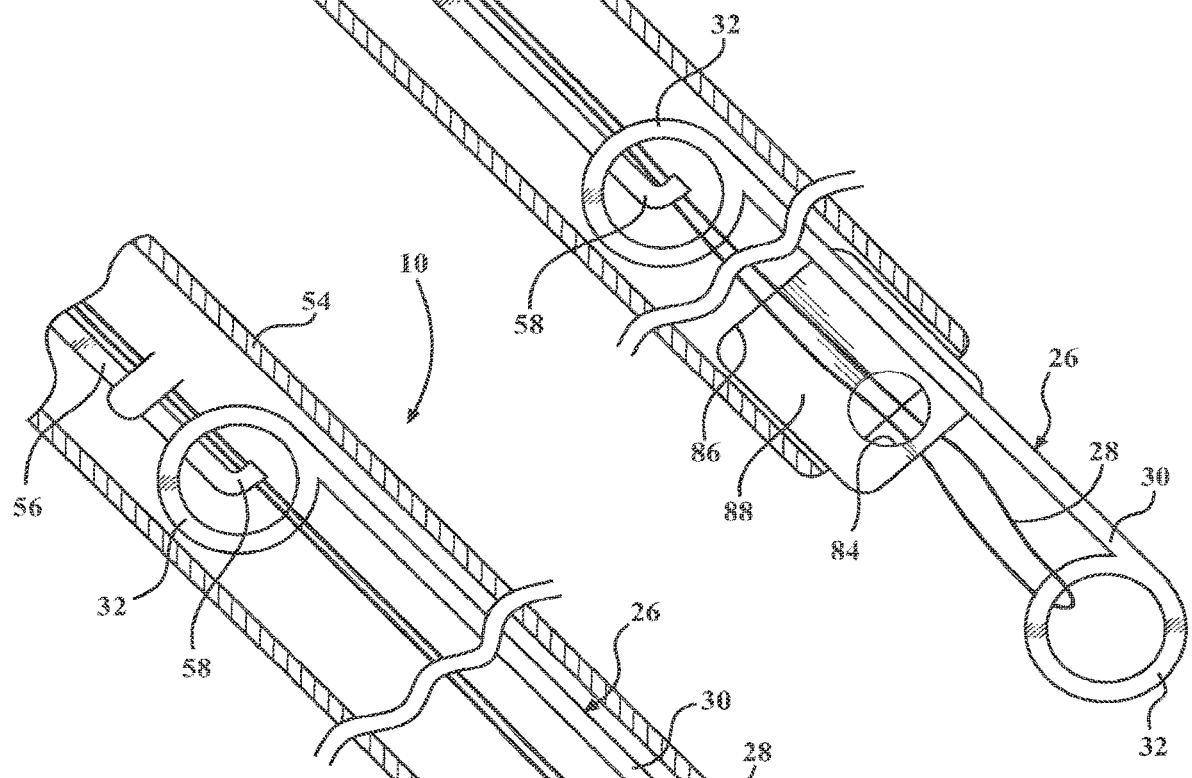
FIG. 11 is a fragmentary view of the CTR inserter of FIG. 7 illustrated in a suture loaded and retracted state.

As illustrated in FIGS. 6B and 6C, further embodiments, according to the present invention of the CTR inserter 10 is shown. In these embodiments, the other end of the suture 28 is also hooked around the trailing eyelet 32 of the CTR 26 before the suture 28 passes through the opening 55 of the cannula 54 of the CTR inserter 10 prior to use. It should be appreciated that the pre-loaded suture 28 of these embodiments may keep the CTR 26 in a more coiled state which may give the surgeon more control to gradually introduce tension in the capsular bag 42. It should also be appreciated that the position of the port 84 has changed axially along the cannula 54 between these embodiments of FIGS. 6B and 6C.

Figure 12:
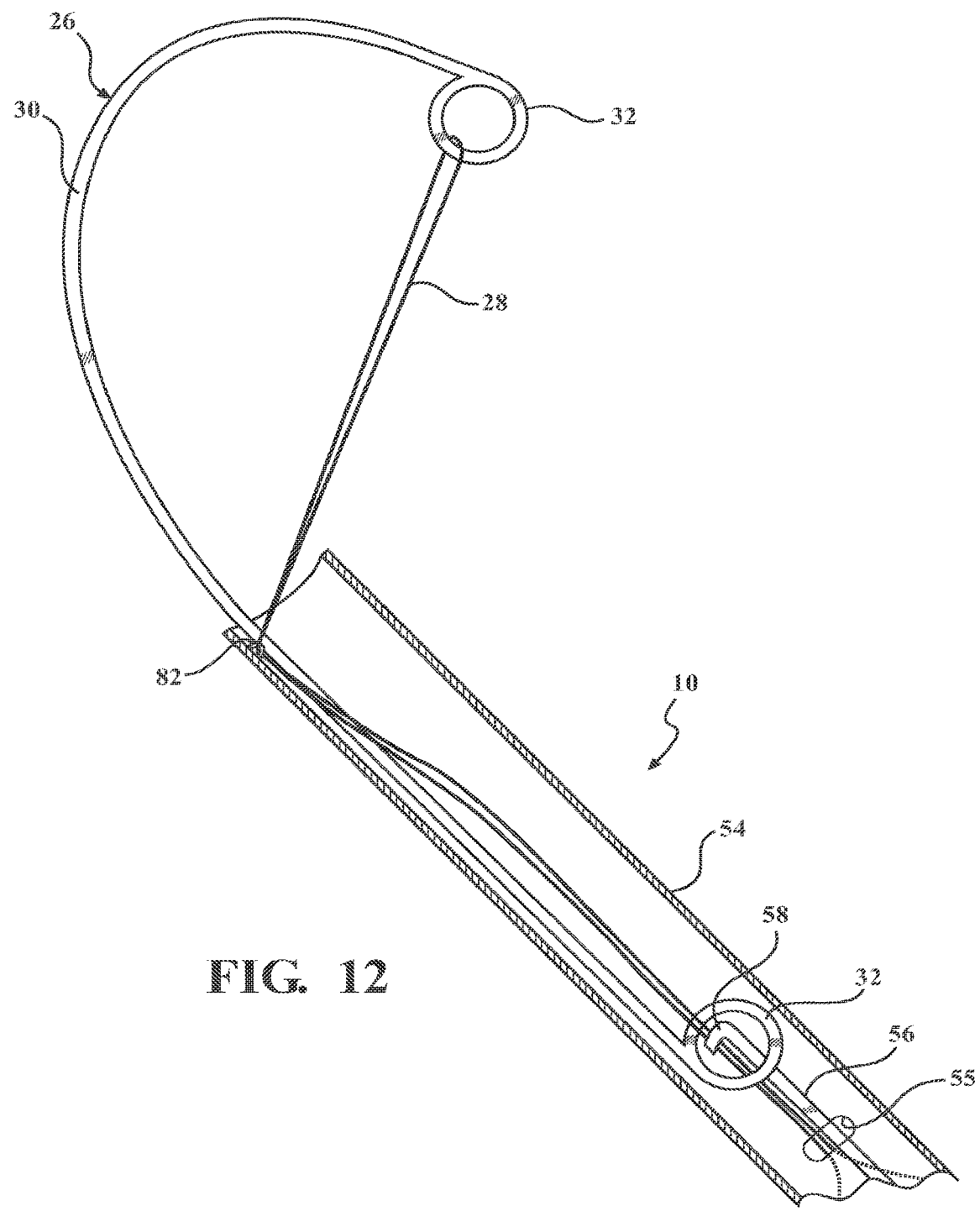
FIG. 12 is a fragmentary view of yet still another embodiment, according to the present invention, of the CTR inserter illustrated in a partially deployed state.

Referring to FIG. 12, yet another embodiment, according to the present invention, of the CTR inserter 10 is shown. In this embodiment, the CTR inserter 10 includes a distal ring element 82 mounted in the cannula 54. The distal ring element 82 guides the suture 28 back through the cannula 54. It should be appreciated that the CTR inserter 10 is similar to that of FIGS. 6-11.

As shown in FIG. 12. as the CTR 26 is deployed from the CTR inserter 10, the suture 28 allows the surgeon to control the position of the CTR 26 in order to mitigate torque forces applied to the fornix of the capsular bag 42 to help prevent iatrogenic zonular damage and vitreous loss with ensuing complications. Specifically, the externalized suture 28 allows the surgeon to apply tension to the leading eyelet 32 of the CTR 26 if any capsular bag displacement is recognized by the surgeon. Tension applied by the surgeon to the leading eyelet 32 is likely to alleviate unwanted torque to the capsular bag 42. As shown, the suture 28 passes through the opening 55 of the cannula 54 of the CTR inserter 10. The port 84 shown in FIG. 6 is of a different configuration than the ports 84 shown in FIGS. 7-11, and it is to be appreciated that the port 84 may be of any suitable configuration and disposed in any suitable location on the cannula 54 of the CTR inserter 10.

Figure 13:
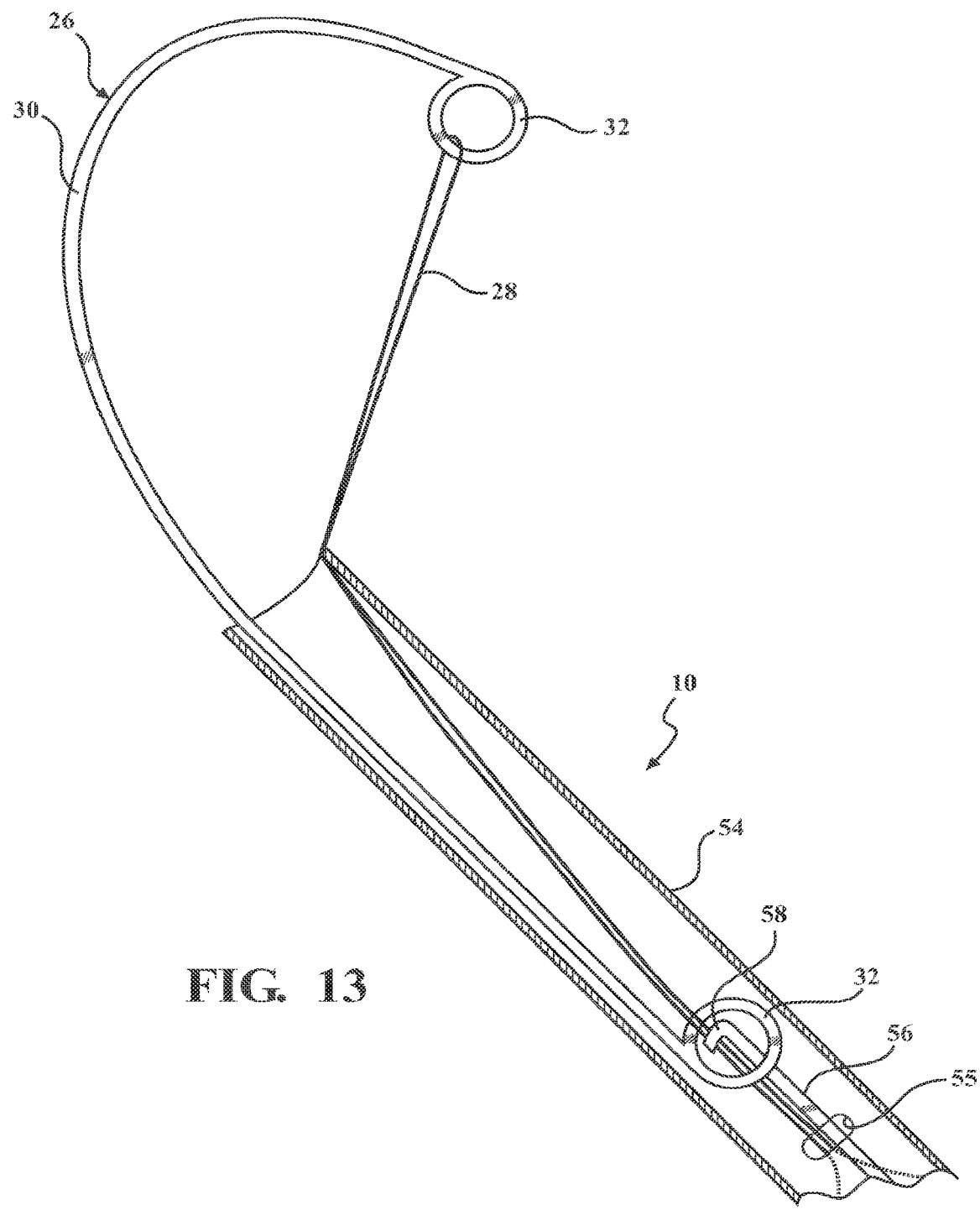
FIG. 13 is a fragmentary view of a further embodiment, according to the present invention of the CTR inserter illustrated in a partially deployed state.
Figure 14:
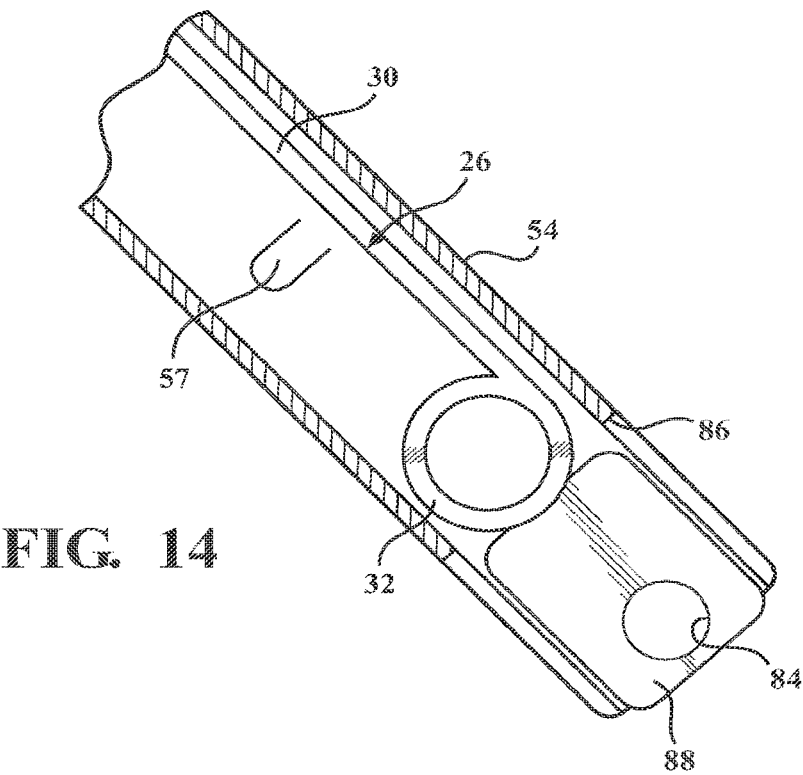
FIG. 14 is a fragmentary view of a yet further embodiment, according to the present invention, of the CTR inserter of FIG. 1 illustrating no side port on a lower flange.
Figure 15:
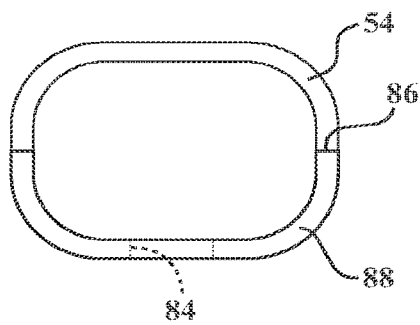
FIG. 15 is a front elevational view of a cannula of the CTR inserter of FIG. 14 illustrating no side port option.
Figure 16:
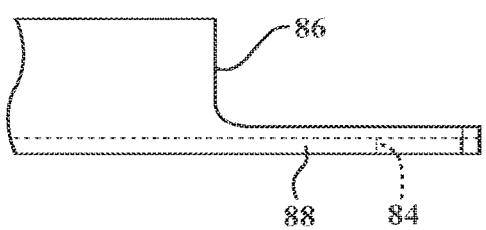
FIG. 16 is a side elevational view of the CTR inserter of FIG. 14 illustrating a flange with a port.
Figure 17:
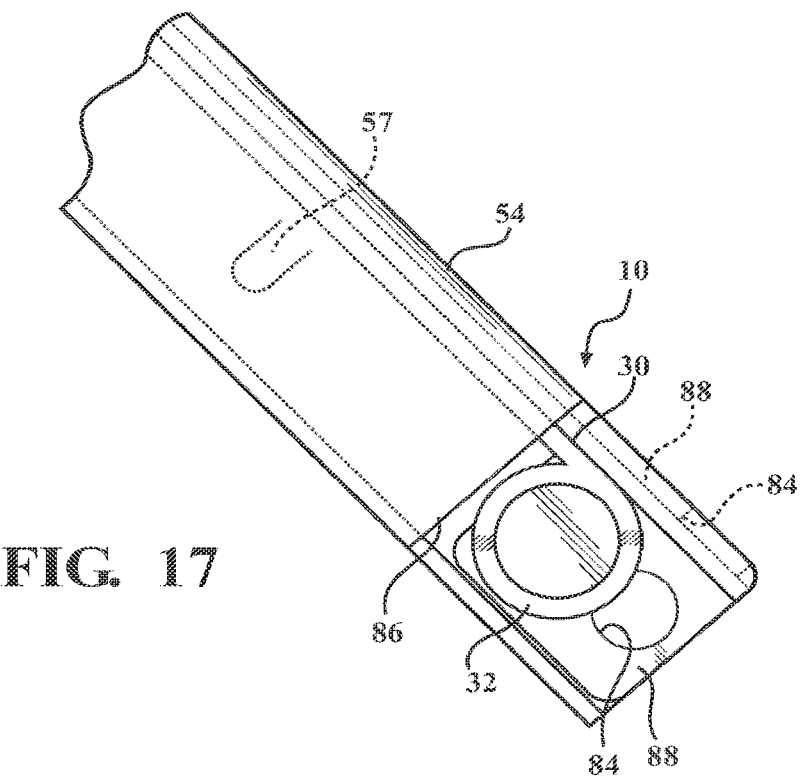
FIG. 17 is a perspective view of a still further embodiment, according to the present invention, of the CTR inserter illustrating a side port option.
Figure 18:
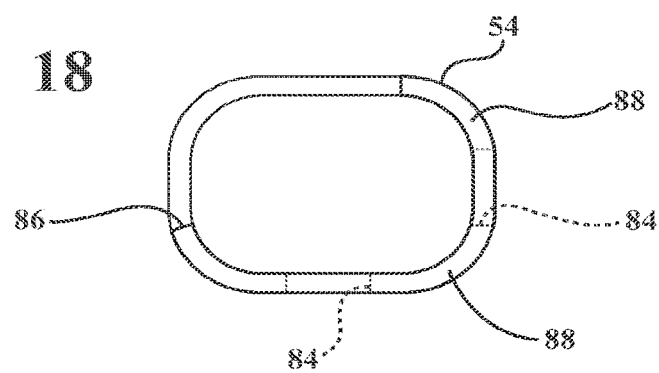
FIG. 18 is a front elevational view of a cannula of the CTR inserter of FIG. 17 illustrating ports on a lower flange of the cannula.
Figure 19:
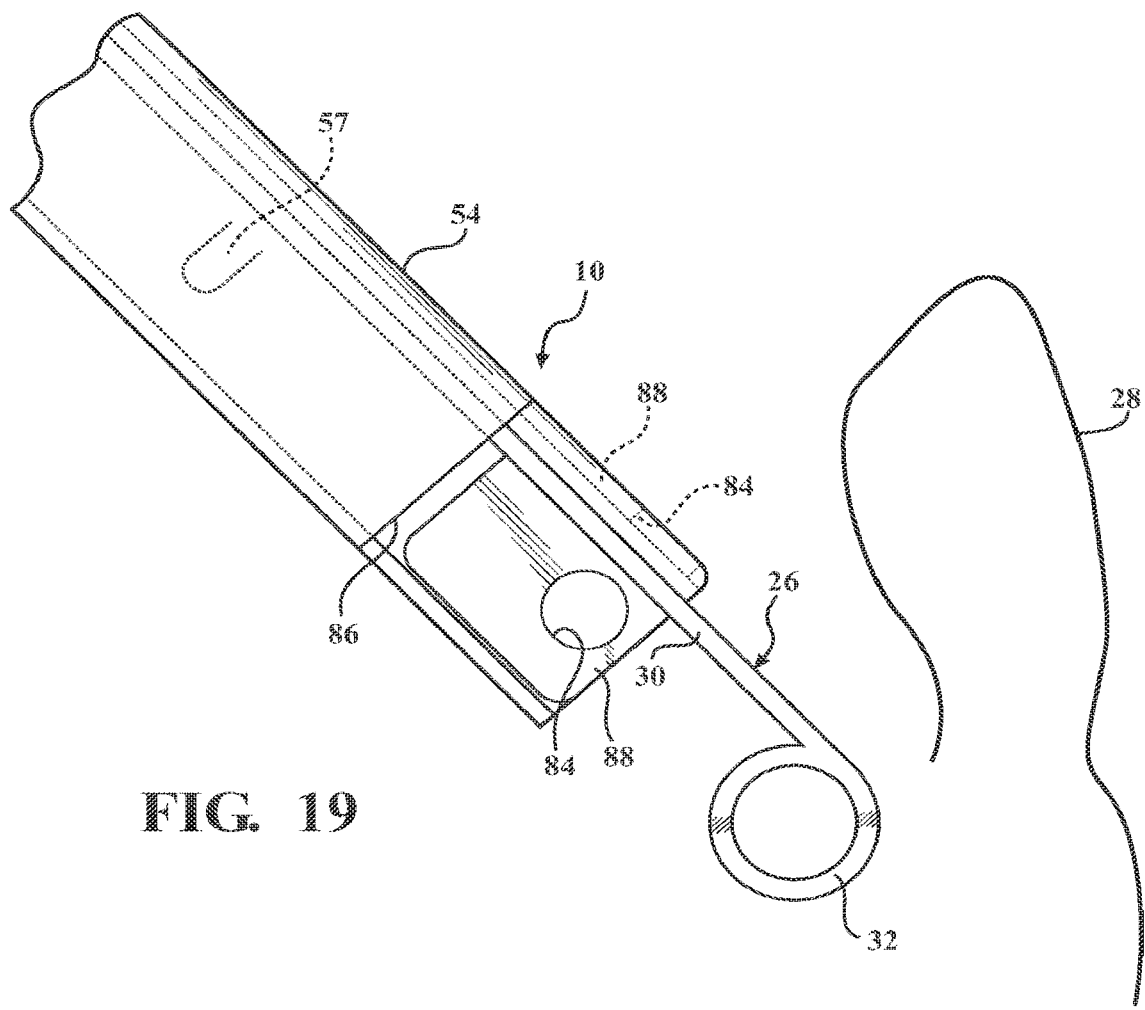
FIG. 19 is a fragmentary view of the CTR inserter of FIG. 17 illustrated in a partially deployed state with a suture beginning to pass through the CTR inserter.
Figure 20:
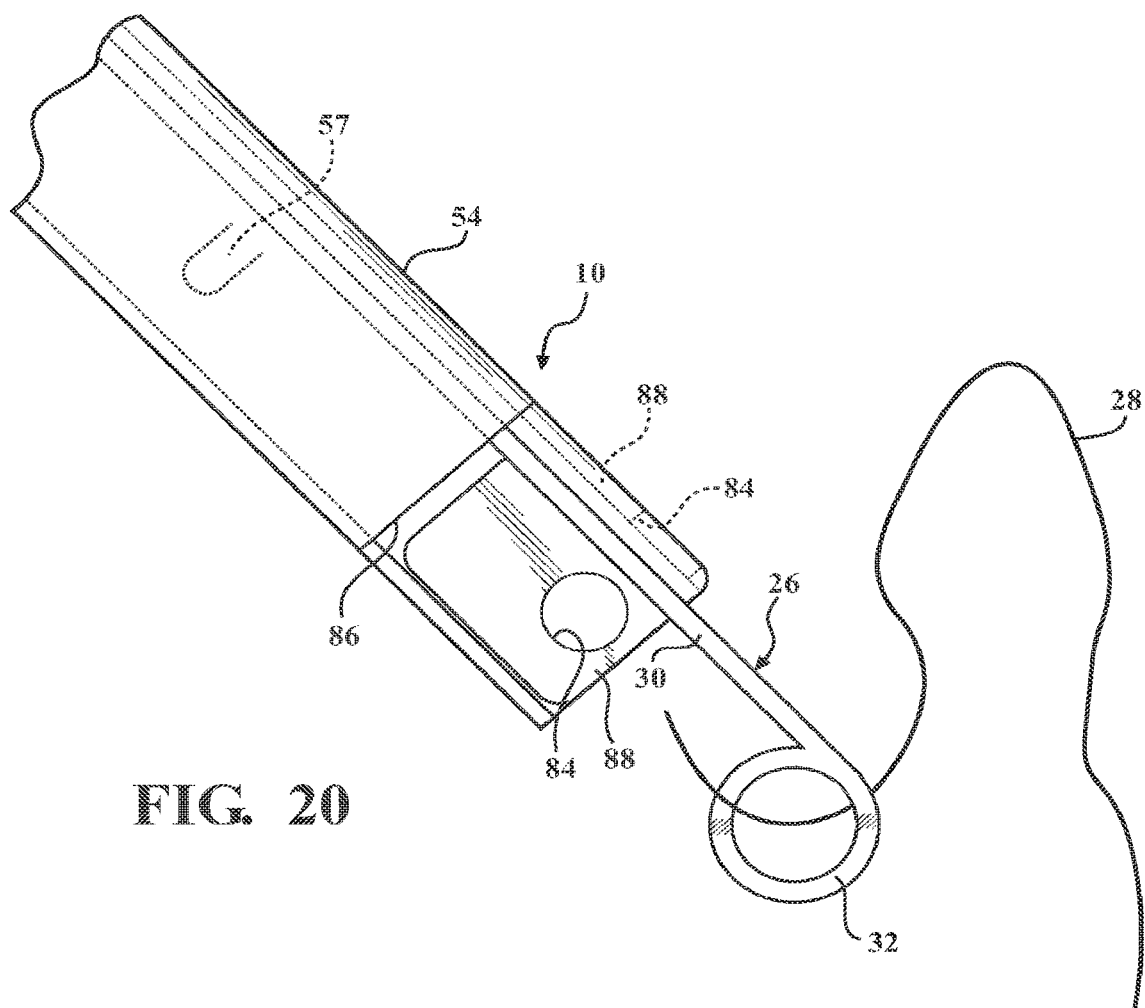
FIG. 20 is a view similar to FIG. 19 of the CTR inserter in a partially deployed state with the suture passed through the CTR and a first end of the suture beginning to pass through a port.
Figure 21:
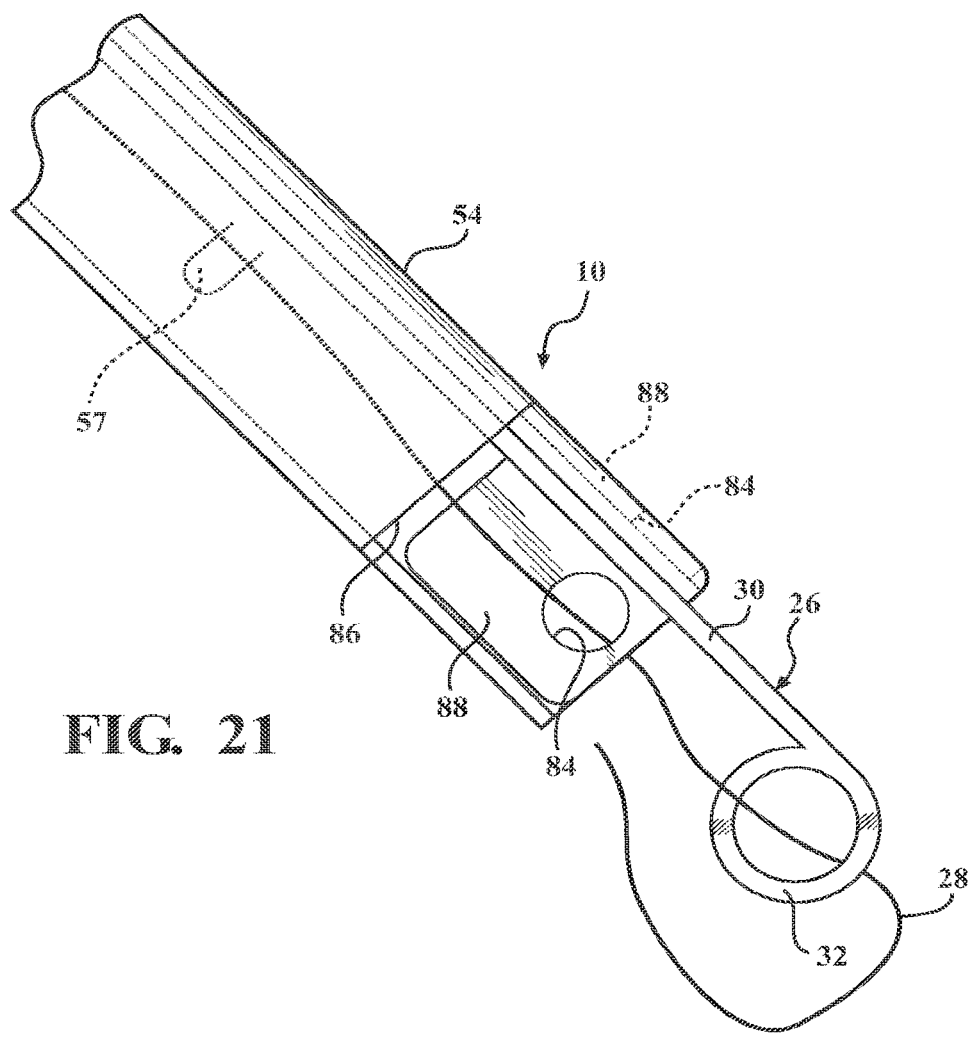
FIG. 21 is a view similar to FIG. 19 of the CTR inserter illustrated in a partially deployed state with the suture passed through the CFR, the first end beginning to pass through the port and a second end passed through the port.

FIG. 13 illustrates yet another alternative embodiment, according to the present invention, of the CTR inserter 10 with the suture 28 abutting an inner wall of the cannula 54 and not passing through a port 84. There is also an opening 55 provided and the suture 28 may or may not pass through the leading eyelet 32 of the CTR 26.

The present invention has been described in an illustrative manner. It is to be understood that the terminology which has been used is intended to be in the nature of words of description rather than of limitation.

It is now apparent to those skilled in the art that many modifications and variations of the present invention are possible in light of the above teachings. It is, therefore, to be understood that the present invention may be practiced otherwise than as specifically described.

What is claimed is:

1. A capsular tension ring inserter (10) comprising:
   a cannula (54) having a wall and a distal end with a port disposed within said wall at said distal end and an opening disposed in said wall spaced from said port;
   a capsular tension ring (CTR) (26) disposed within said cannula (54) and having a leading eyelet (32);
   an element (56) disposed within said cannula (54) that engages and moves said CTR (26) during deployment; and
   a suture (28) placed on said leading eyelet (32) and fed through said port, into said cannula (54), and through said opening out of said cannula to allow a user to control said CTR (26) by pulling on said suture (28) exiting said cannula for controlled deployment of said CTR (26).

2. A capsular tension ring inserter (10) as set forth in claim 1 wherein said element (56) has a hook end (58) to engage said CTR (26).

3. A capsular tension ring inserter (10) as set forth in claim 1 wherein said cannula (54) includes a notch (86) defining a flange (88) extending outwardly therefrom with said port (84) disposed within said flange (88).

4. A capsular tension ring inserter (10) as set forth in claim 1 wherein said port and said opening are spaced from each other along said cannula.

5. A capsular tension ring inserter (10) as set forth in claim 1 wherein said port and said opening are located on opposing sides of said cannula.

6. A capsular tension ring inserter (10) as set forth in claim 1 wherein said CTR has a trailing eyelet (32) with said suture (28) being placed on said trailing eyelet (32) before exiting said cannula through said opening.

7. A capsular tension ring inserter (10) comprising:
   a capsular tension ring (CTR) (26) having a leading eyelet (32);
   a cannula (54) housing said CTR (26) with said cannula having a wall and a distal end with a port disposed within said wall at said distal end and an opening disposed in said wall spaced from said port;
   an element (56) disposed within said cannula (54) that engages and moves said CTR (26) during deployment; and
   a pre-loaded suture (28) placed on said leading eyelet (32), passing through said port and exiting said cannula (54) through said opening to allow a user to control insertion of said CTR (26) into a capsular bag (42) of an eye (40) by pulling on said suture (28) during insertion of said CTR (26).

8. A capsular tension ring inserter (10) as set forth in claim 7 wherein said cannula (54) includes a notch (86) defining a flange (88) extending outwardly therefrom with said port (84) disposed within said flange (88).

9. A capsular tension ring inserter (10) as set forth in claim 7 wherein said port and said opening are spaced from each other along said cannula.

10. A capsular tension ring inserter (10) as set forth in claim 7 wherein said port and said opening are located on opposing sides of said cannula.

11. A capsular tension ring inserter (10) as set forth in claim 7 wherein said CTR has a trailing eyelet (32) with said suture (28) being placed on said trailing eyelet (32) before exiting said cannula through said opening.

12. A method of operating a capsular tension ring inserter (10) having a cannula (54) with the cannula having a wall and a distal end with a port disposed within the wall at the distal end and an opening disposed in the wall spaced from the port, and the cannula housing a capsular tension ring (CTR) (26) having a leading eyelet (32) and an element (56) disposed within the cannula (54) with a suture (28) placed on the leading eyelet (32) and fed back through the cannula and out through the opening, said method comprises the steps of;
   moving the CTR (26) to a partially deployed position; and
   controlling the leading eyelet (32) with the suture (28) during insertion of the CTR (26) in a capsular bag (42) of an eye (40) by allowing a user to pull on the suture

(28) exiting the opening with the suture tensioning against the port during insertion of the CTR (26).

13. A method as set forth in claim 12 including the steps of moving the CTR (26) to a fully deployed position and lifting the element (56) out of a trailing eyelet (32) of the CTR (26).

14. A method as set forth in claim 12 including the step of holding a trailing portion of the a second end of the suture (28) in place by a suture hold on or inside the cannula (54).

15. A method as set forth in claim 12 further including the step of moving the element (56) into engagement with the CTR (26) in order to move the CTR (26) to a deployed position.

16. A method of pre-loading a capsular tension ring (CTR) inserter (10) with a suture (28) where the CTR inserter has a cannula (54) housing a capsular tension ring (CTR) (26) with the cannula having a wall and a distal end with a port disposed within the wall at the distal end and an opening disposed in the wall spaced from the port, said method comprising the steps of:

moving the CTR (26) to a position outside of the cannula with at least a leading eyelet (32) of the CTR positioned outside of the cannula;

placing the suture (28) on the leading eyelet (32) of the CTR (26) while the CTR is outside the cannula;

feeding the suture (28) through the port in the cannula;

feeding the suture along the cannula to the opening;

feeding the suture through the opening out of the cannula;

retracting the CTR (26) into the CTR inserter (10) to define a pre-loaded condition with the suture (28) remaining looped around the leading eyelet (32) of the CTR (26) and remaining through the port and the opening when in the pre-loaded condition to allow a user to control the leading eyelet of the CTR (26) during deployment of the CTR (26).

\* \* \* \* \*